(12) United States Patent
Cunningham et al.

(10) Patent No.: US 8,106,019 B2
(45) Date of Patent: Jan. 31, 2012

(54) CHEC-7 A NOVEL SPLA2 INHIBITOR

(75) Inventors: Timothy J. Cunningham, Fort Washington, PA (US); Lihua Yao, Wynnewood, PA (US); Jeffrey I. Greenstein, Philadelphia, PA (US)

(73) Assignee: Philadelphia Health & Education Corporation, Philadelphia, PA (US)

( * ) Notice: Subject to any disclaimer, the term of this patent is extended or adjusted under 35 U.S.C. 154(b) by 606 days.

(21) Appl. No.: 11/974,527

(22) Filed: Oct. 12, 2007

(65) Prior Publication Data

US 2008/0249027 A1    Oct. 9, 2008

Related U.S. Application Data

(63) Continuation-in-part of application No. 10/714,699, filed on Nov. 17, 2003, now Pat. No. 7,528,112.

(60) Provisional application No. 60/426,536, filed on Nov. 15, 2002, provisional application No. 60/697,598, filed on Jul. 8, 2005.

(51) Int. Cl.
*C07K 7/06* (2006.01)
*A61K 38/08* (2006.01)

(52) U.S. Cl. ........................ 514/21.7; 530/329

(58) Field of Classification Search ........................ None
See application file for complete search history.

(56) References Cited

U.S. PATENT DOCUMENTS 6,262,024 B1    7/2001    Cunningham et al.

OTHER PUBLICATIONS

NCBI Accession No. XP_819598, submitted Jul. 2005. Retrieved [online] on Mar. 22, 2010. Retrieved from: <http://www.ncbi.nlm.nih.gov/protein/71665253>.*

Jackowski, British Journal of Neurosurgery 9: (1995) 303-317.*
Rudinger, In "Peptide Hormones" (ed., J.A. Parsons) University Park Press, Baltimore, pp. 1-7 (1976).*
Mihelich et al., Structure-based design of a new class of anti-inflammatory drugs: secretory phospholipase $A_2$ inhibitors, SPI, Biochimica et Biophysica Acta 1441 (1999), pp. 223-228.
Springer, D, Aan Update on Inhibitors of Human 14kDa Type II s-PL$A_2$ in Development, Current Pharmaceutical Design (2001), vol. 7, pp. 181-198.
Abraham et al., Efficacy and safety of LY315920Na/S-5920, a selective inhibitor of 14-kDa group IIa secretory phospholipase $A_2$, in patients with suspected sepsis and organ failure, Criticial Care Medicine, (2003) vol. 31, No. 3, pp. 718-728.
Eagleson, et al., Rescue of Both Rapidly and Slowly Degenerating Neurons in the Dorsal Lateral Geniculate Nucleus of Adult Rats by a Cortically Derived Neuron Survival Factor, Experimental Neurology, (1992) vol. 116, pp. 156-162.
Eagleson et al., Different Populations of Dorsal Lateral Geniculate Nucleus Neurons Have Concentration-Specific Requirements for a Cortically Derived Neuron Survival Factor, Experimental Neurology, (1990), vol. 110: pp. 284-290.
Paterson et al., α-Cardiac Actin is the Major Sarcomeric Isoform Expressed in Embryonic Avian Skeletal Muscle, Science (1984), vol. 224, pp. 1436-1438.
Cunningham et al., Identification of a Survival-Promoting Peptide in Medium Conditioned by Oxidatively Stressed Cell Lines of Nervous System Origin, The Journal of Neuroscience (1998), vol. 18, No. 18., pp. 7047-7060.
Cunningham et al., Identification of the Human cDNA for New Survival/Evasion Peptide (DSEP): Studies in Vitro and in Vivo of Overexpression by Neural Cells, Experimental Neurology (2002), vol. 177, pp. 32-39.
Cunningham et al., Calreticulin Binding and Other Biological Activities of Survival Peptide Y-P30 Including Effects of Systemic Treatment of Rats, Experimental Neurology (2000), vol. 163, pp. 457-468.

* cited by examiner

*Primary Examiner* — Robert C Hayes
(74) *Attorney, Agent, or Firm* — Riverside Law LLP

(57) ABSTRACT

The present invention relates to the discovery of a composition including a seven-amino acid peptide that promotes neuronal survival, inhibits inflammation, and is a potent inhibitor of sPL2A, and uses thereof.

4 Claims, 15 Drawing Sheets

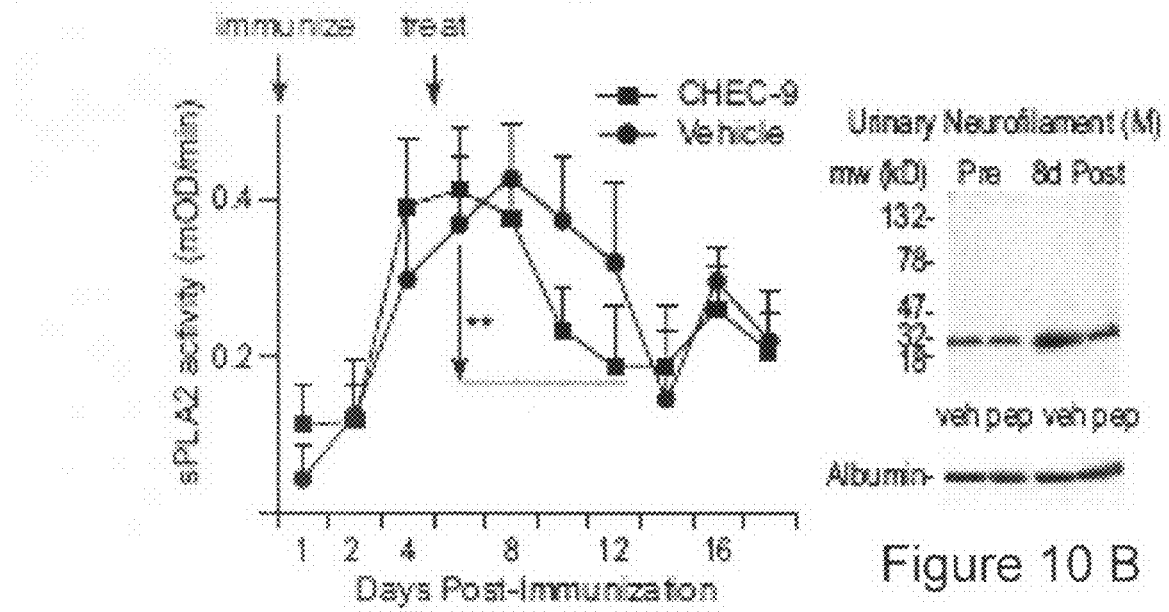
Figure 10
Figure 10 A
Figure 10 B
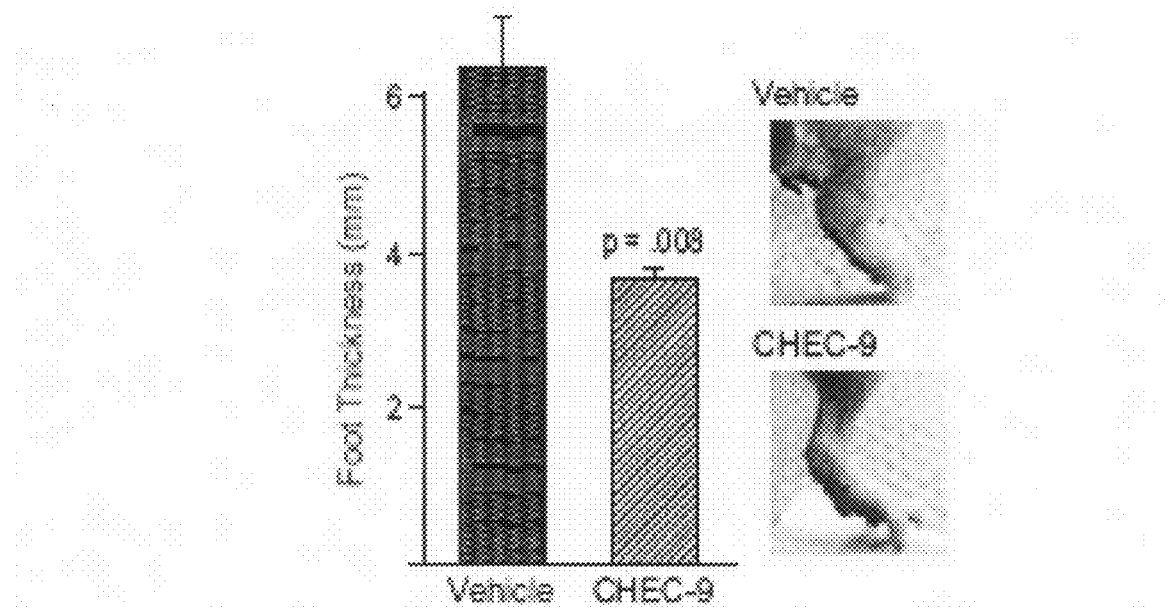
Figure 11

Figure 14
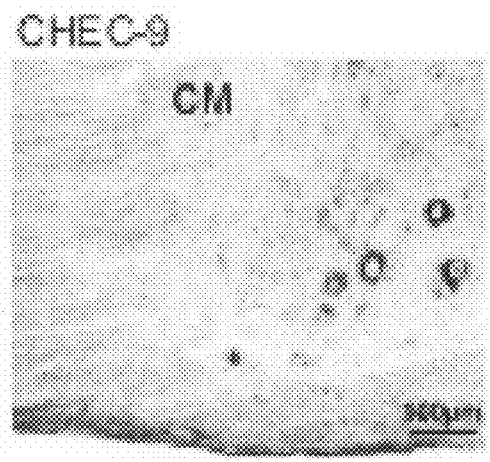
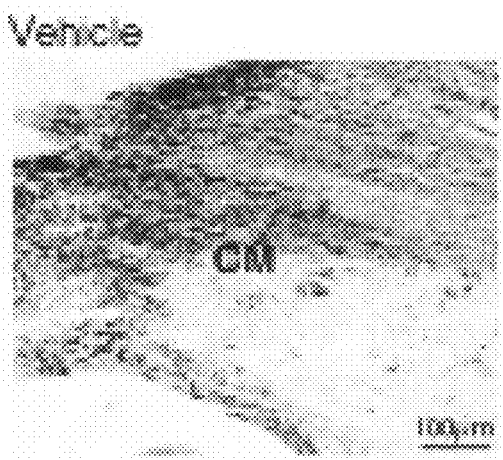
Figure 14 A    Figure 14 B

Figure 16
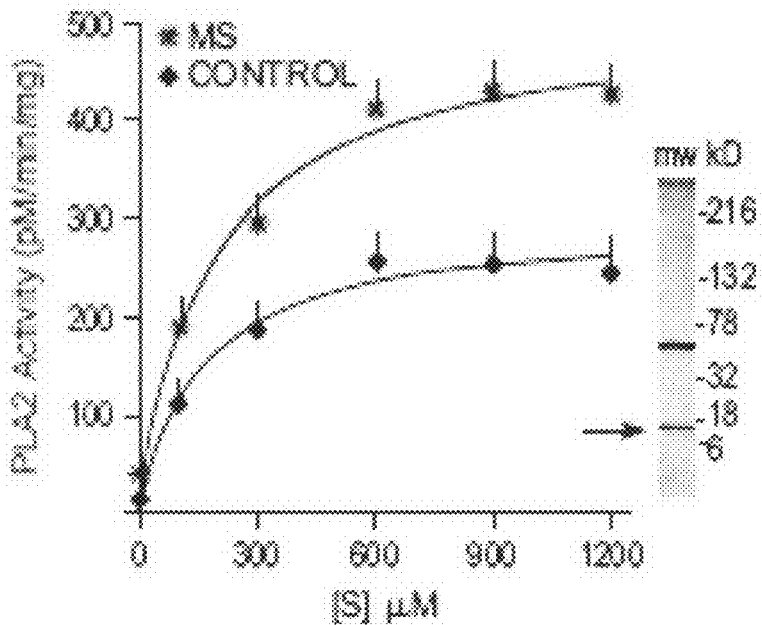
Figure 16 A
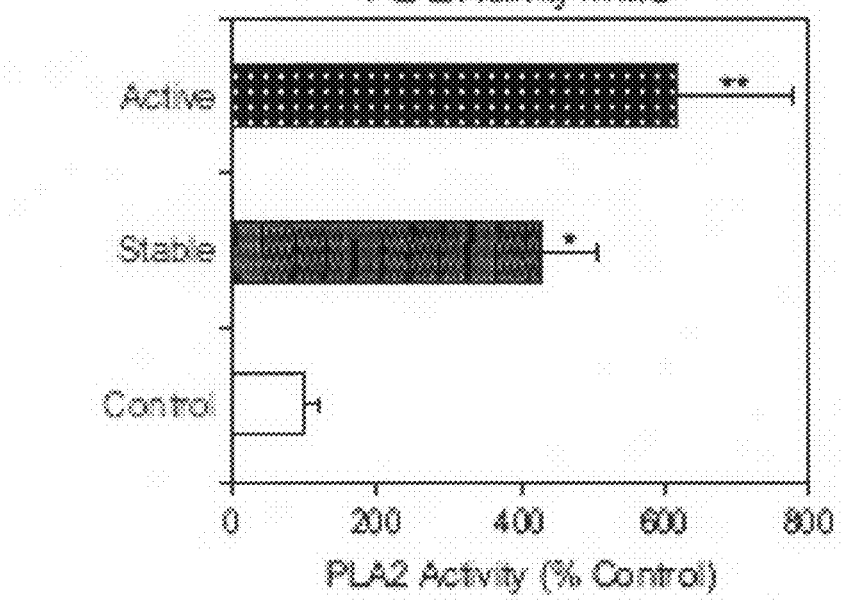
Figure 16 B

Figure 17
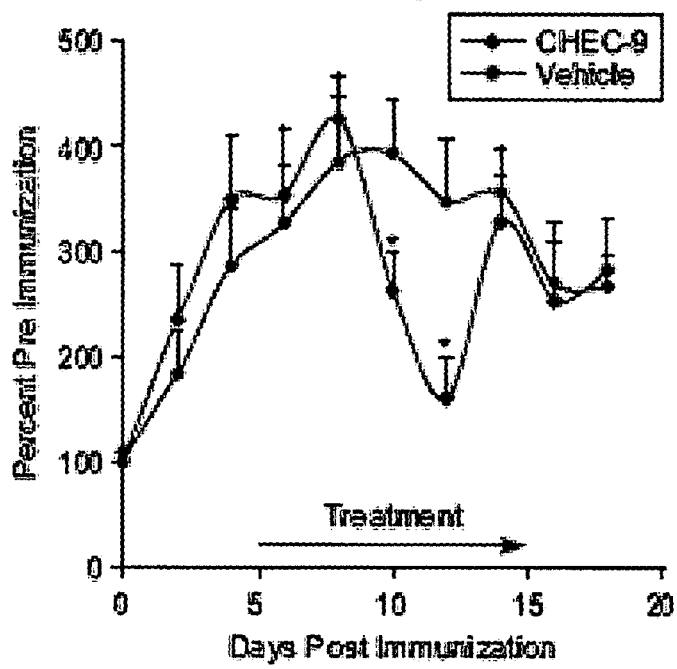
Figure 17A
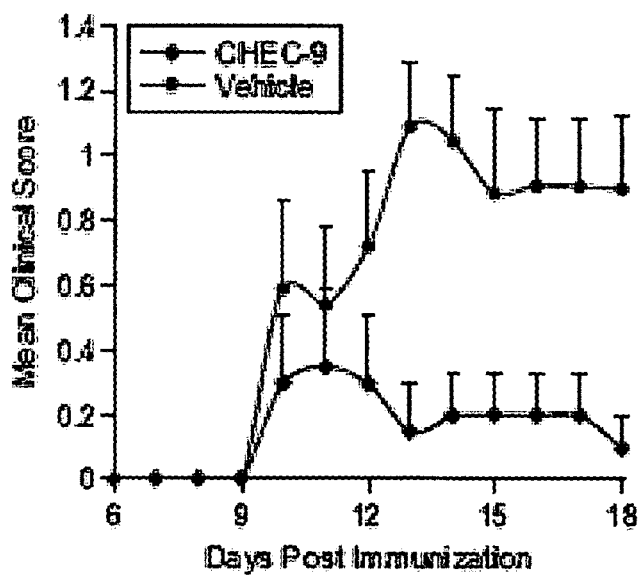
Figure 17B

CHEC-7 A NOVEL SPLA2 INHIBITOR

CROSS-REFERENCE TO RELATED APPLICATIONS

This application is a continuation-in-part of U.S. patent application Ser. No. 10/714,699, filed Nov. 17, 2003, which claims priority to U.S. Provisional Patent Application No. 60/426,536, filed Nov. 15, 2002 and this application also claims priority to United States International Application No. PCT/US2006/26568 filed Jul. 10, 2006 which claims priority to U.S. Provisional Patent Application No. 60/697,598 filed Jul. 8, 2005 all of which are incorporated by reference herein in their entirety.

STATEMENT REGARDING FEDERALLY SPONSORED RESEARCH OR DEVELOPMENT

This invention was made, in part, using funds obtained form the U.S. Government (National Institutes of Health Grant No. NS16347, and the U.S. Government therefore has certain rights in this invention.

BACKGROUND OF THE INVENTION

Neurotrophic factors are considered to be vital for normal development of the nervous system. During development, neuronal target structures produce limited amounts of specific neurotrophic factors necessary for both the survival and differentiation of neurons projecting into the structures. The same factors have been found to be involved in the survival and/or maintenance of mature neurons.

A neurotrophic factor is defined as a substance capable of increasing and/or maintaining survival of a neuron population, and possibly affecting outgrowth of neurites (neuron processes) and certain other metabolic activities of a neuron. Neurotrophic factors are generally described as soluble molecules synthesized in the peripheral targets of neurons and transported to their cell bodies, where they exert their effects.

Studies with isolated neurotrophic factors have shown that exogenously added neurotrophic factors can exert their neurotrophic effects upon cultured neurons in vitro, or by administration to damaged or degenerated neurons in vivo. For this reason, various neurotrophic factors have received great attention as potential therapeutic agents for treatment of degenerative diseases of the central nervous system, as well as traumatic damage to the CNS. For example, nerve growth factor (NGF) has been shown to increase the survival, function and regeneration of cholinergic neurons in the basal forebrain. Degeneration of this population of cholinergic neurons has been associated with patients having Alzheimer's disease, and could be the primary neuronal defect responsible for the loss of cognitive function associated with Alzheimer's disease. NGF has been found to be synthesized and released from the target areas of these cholinergic neurons in the hippocampus and neurocortex, both areas of the brain associated with learning and memory. See Springer, J. E., Drug News and Perspectives, 4: 394-99 (1991). As another example, a dopaminergic neurotrophic factor (DNTF) has been purified and characterized, and found to promote survival and neurite outgrowth of dopaminergic neurons of the substantia nigra. DNTF is considered a potentially valuable therapeutic agent for the treatment of Parkinson's disease which involves degeneration of dopaminergic motor neurons of the central nervous system (U.S. Pat. No. 5,215,969 to Springer et al., 1993).

It can be seen from the foregoing examples that neurotrophic factors are a valuable source of therapeutic agents for the treatment of neuron damage and neurodegenerative disease. However, the development of such factors as therapeutic agents can be problematic. For example, it is difficult to determine the specificity of an endogenous neurotrophic agent, i.e., whether different factors exist for different nervous system pathways, and which neuron populations in those pathways are affected by a factor. In fact, many identified neurotrophic agents have been shown to have a wide range of biological functions, acting on both central and peripheral neurons, as well as non-neuronal cells in vitro (e.g., polypeptide growth factors and ciliary neurotrophic factor, CNTF). In the central nervous system, with its complex interconnections and heterogeneous neuron types, it is difficult to determine which neurotrophic factors are effective on a particular neuronal population. This difficulty is further exacerbated by the fact that many of the neurotrophic factors that have been characterized have been found to be closely related to one another. For example, it is now known that NGF possesses amino acid sequence homology to brain-derived neurotrophic factor (BNDF), a protein with similar, but not identical, in vitro properties as NGF (Barde et al., 1982, EMBO J., 1: 549-53; Leibrock et al., Nature, 1989, 341: 149-52). In fact, NGF, BNDF and the neurotrophin (NT) series have been classified as members of a superfamily of neurotrophic factors (NGF superfamily). Because of their similarity in amino acid sequence (and hence nucleotide sequences encoding the factor), it has been difficult to develop nucleic acid or antibody probes that are specific for a particular member of the family. The lack of a specific means for identifying a particular neurotrophic factor has hindered the elucidation of particular neuronal populations affected by a specific factor.

An additional obstacle to developing neurotrophic factors as therapeutic agents for treatment of damaged neurons is that few in vivo models exist to study the survival-promoting activity of these factors in the central nervous system. In order to develop a neurotrophic factor as an effective therapeutic agent for the treatment of neuron degeneration, it is important to be able to determine where in the central nervous system the neurotrophic factor operates, whether the treatment with exogenous neurotrophic factor is effective, and the concentration of neurotrophic factor effective for imparting a therapeutic effect. Such an objective would best be accomplished with a neurotrophic factor that is identifiable and distinct from other factors, that is capable of exerting an effect on many different neuron populations, and for which in vivo models are available to test the efficacy of the neurotrophic factor on a specific neuron population.

The neuron survival-promoting peptide Y-P30 was originally identified in the secretions of neural cells (neuroblastoma and retinoblastoma) subjected to oxidative stress (Cunningham, et al. 1998, J. Neurosci. 18:7047-7060). Partially purified fractions of conditioned culture medium were screened in vitro until the active Y-P30 peptide was identified—the synthetic version of this peptide was then tested in vitro and in vivo and found to support neural cells which were degenerating for a variety of reasons, including oxidative stress and central nervous system trauma (Cunningham, et al. 1998, J. Neurosci. 18:7047-7060; Cunningham et al., 2000, Exp. Neurol. 163:457-468). This peptide was later confirmed to be part of an endogenous human polypeptide (~12 kiloDaltons) named DSEP after identification of the human cDNA encoding DSEP and the locus of the DSEP gene in human chromosomal region 12q (Cunningham, et al. 2002, Exp. Neurol. 177:32-39). In that study, it was found that overexpression of the full length polypeptide in neural cells made them resistant to several forms of oxidative stress including that resulting from immune cell attack.

The contribution of inflammatory cells and their secretions to cell death after CNS injury or in neurodegenerative disorders is for the most part well established (Stoll, et al., 1998, Prog. Neurobiol. 56:149-171). The principal immune cell participants in the response to traumatic CNS injury are monocyte derivatives (microglia/macrophages). These cells are the source of a number of inflammatory agents that may contribute to neuron death, including superoxide anion, nitric oxide, IL-1P, and TNFα (reviewed by Rothwell, et al 1996, Pharm. Ther. 69:85-95; Stoll et al 1998, Prog. Neurobiol. 56:149-171; Jander, et al 1998, Eur. J. Neurosci. 10:680-688; Turrin, et al 2001, (Brain Res. Bull. 54:443-53). TNFα is best known for its cytotoxic activity outside the nervous system, but also has pronounced toxic activity on neural cells after brain injury (Barone, et al., 1997, Stroke 28:1233-1244; Lavine, et al., 1998, J. Cereb. Blood Flow Metab. 18:52-58). Both overexpression of the full length DSEP molecule and application of Y-P30 inhibits the appearance and differentiation of macrophages and microglia (Cunningham, et al. 1998, J. Neurosci. 18:7047-7060; Cunningham et al., 2000, Exp. Neurol. 163:457-468; Cunningham, et al. 2002, Exp. Neurol. 177:32-39).

Steroid anti-inflammatory drugs currently used to treat nervous system injury and other disorders with an inflammatory component operate in part by stimulating the production of endogenous inhibitors of phospholipases (A2) (PLA2) which are the enzymes responsible for the production of several lipid mediators of inflammation (Flower, R J et al., 1979, Nature 278:456-459). PLA2 enzymes and downstream participants in this pathway play a role in chronic neurodegenerative disorders including Alzheimer's disease (Farooqui A A, et al., 1999, Brain Res. Bull. 49:139-153; Hull M, et al., 2002, Curr. Med. Chem. 9:83-88).

Multiple sclerosis (MS) is a debilitating, inflammatory, neurological illness characterized by demyelination of the central nervous system. The disease primarily affects young adults with a higher incidence in females. Symptoms of the disease include fatigue, numbness, tremor, tingling, dysesthesias, visual disturbances, dizziness, cognitive impairment, urological dysfunction, decreased mobility, and depression. Four types classify the clinical patterns of the disease: relapsing-remitting, secondary progressive, primary-progressive and progressive-relapsing (S. L. Hauser and D. E. Goodkin, Multiple Sclerosis and Other Demyelinating Diseases in Harrison's Principles of Internal Medicine 14$^{th}$ Edition, vol. 2, McGraw-Hill, 1998, pp. 2409-2419).

Recent studies with rodent Experimental Autoimmune Encephalitis (EAE) models of Multiple Sclerosis (MS) suggest phospholipase A2 (PLA2) enzymes are involved in the genesis of both the behavioral deficits and the inflammation that characterize this disease (Pinto, et al., 2003, Glia 44:275-282; Kalyvas and David, 2004, Neuron 41:323-335). Systemic sPLA2 enzymes in particular were inhibited in one of these studies by infusion of large molecule sPLA2 substrate decoys. The result was significant behavioral improvement and reduced inflammation.

The exact etiology of MS is unknown; however, it is strongly suspected that the demyelination characteristic of the disease is the result of an autoimmune response, perhaps triggered by an environmental insult, e.g. a viral infection. The pathophysiology of Multiple Sclerosis involves both antigen specific mechanisms and the innate immune system, including several elements of the inflammatory response. MS is not unusual in this regard since inflammation is now recognized as a contributing factor in all disorders in which there is destruction of nervous tissue. Increased hydrolysis of membrane phospholipids by phospholipase A2 is a well-known early response to tissue damage in all organ systems including the nervous system. The activity of these enzymes regulates levels of inflammatory mediators including prostaglandins, leukotrienes, fatty acids, and reactive oxygen species. All these mediators are produced in the early stages of neurodegeneration, regardless of its cause. However, the role of PLA2 activity and many of these downstream PLA2 products has received relatively little attention.

At the present time, there is no cure for MS. Current therapies are aimed at alleviating the symptoms of the disease and arresting its progress. Depending upon the type, drug treatment usually entails the use of disease-modifying agents such as the interferons (interferon beta 1-a, beta 1-b and alpha 2), glatiramer acetate or corticosteroids such as methylprednisolone and prednisone. Also, chemotherapeutic agents, such as methotrexate, azathioprine, cladribine, cyclophosphamide and cyclosporine, have been used. All of the above treatments have side-effect liabilities, little or no effect on fatigue and depression, as well as limited effects on relapse rates and on ability to prevent exacerbation of the disease. Treatment with interferons may also induce the production of neutralizing antibodies, which may ultimately decrease the efficacy of this therapy.

CHEC-9 is an anti-inflammatory and neuron survival-promoting peptide. In the first instance, it inhibits enzymes that initiate a cascade of changes during the early stages of inflammation, so like other drugs that operate in this pathway (e.g. the COX inhibitors), it may have minimal effects on critical functions of the acquired immune response. On the other hand, it is possible that elimination of the early inflammatory component of MS will limit subsequent events in the cascade such as effusion of immune cells, myelin and axonal degeneration, and thereby inhibit active disease. In addition, the direct cell survival-promoting properties of CHEC-9 may further indicate its potential efficacy in MS, especially in light of new models of the disease that highlight the primary importance of cell degeneration (both neuronal and oligodendrocytic).

Recent studies of rodent experimental autoimmune encephalomyelitis (EAE) models of MS suggest PLA2 enzymes are involved in the genesis of both the behavioral deficits and the inflammation that characterize this disease. Pinto, et al. report that systemic infusion of substrate-like molecules, presumably targeting secreted (s)PLA2s, is effective in reducing inflammation and clinical EAE disease. However, the status of MS patients with regard to PLA2 activity is unknown, so it is not clear whether these enzymes are indeed a worthwhile target for MS treatment.

Therefore, a need exists in the art for identification and testing in vivo of new neurotrophic factors which are distinct from other factors, exert an effect on many different neurons, and/or which can act as PLA2 inhibitors, to facilitate the development of new therapies for neurodegenerative disorders, such as MS, and for other diseases with an inflammatory component.

BRIEF SUMMARY OF THE INVENTION

One embodiment of the present invention comprises an isolated neuron survival-promoting peptide, CHEC-7, having the sequence of CHEASQC (SEQ ID NO: 3) or a variant thereof, wherein the peptide promotes neuron survival, inhibits the brain's immune response to degenerating elements, and/or inhibits phospholipase A2. The peptide may be linearized or cyclized. Another aspect of the invention includes variants of the CHEC-7 peptide having 1-7 conservative amino acid substitutions, wherein the peptide promotes neuron survival, inhibits the brain's immune response to degenerating elements, and/or inhibits phospholipase A2. Another aspect of the invention comprises a pharmaceutical preparation comprising the neuron survival-promoting peptide CHEC-7, in a biologically acceptable carrier.

Another embodiment of the present invention includes a method for treating a patient having a neurodegenerative disorder, or disorder with an inflammatory component comprising administering to the patient a therapeutically effective amount of a CHEC-7 peptide. In one aspect, the neurodegenerative disorder is selected from the group consisting of trauma, stroke, nonspecific anoxia, mental retardation syndromes associated with progressive neuronal degeneration, and a neurodegenerative disease. In another aspect, the neurodegenerative disease is selected from the group consisting of Multiple Sclerosis (MS), Alzheimer's disease, Parkinson's disease, and amyotrophic lateral sclerosis (ALS). In still another aspect, the disorder with an inflammatory component is selected from the group consisting of asthma, autoimmune disease, and allergies.

Yet another embodiment of the present invention includes a method for treating a patient having an acute head trauma or neural injury comprising administering to the patient a therapeutically effective amount of a CHEC-7 peptide. In one aspect of the invention, a CHEC-7 peptide is administered at a time point selected from the group consisting of within 1 hour of injury, within 2 hours of injury, within 6 hours of injury, within 12 hours of injury, and within 1 day of injury. In another aspect of the invention, a CHEC-7 peptide is administered in combination with another therapeutic agent.

Another embodiment of the present invention includes an isolated nucleic acid molecule encoding a CHEC-7 peptide (SEQ ID NO.3). One aspect of the present invention includes an isolated RNA molecule transcribed from the nucleic acid encoding a CHEC-7 peptide. Still another aspect of the present invention includes an isolated plasmid comprising the nucleic acid encoding a CHEC-7 peptide. Yet another aspect of the invention includes an isolated vector comprising the nucleic acid molecule encoding a CHEC-7 peptide. A further aspect of the invention includes an isolated retroviral vector comprising the nucleic acid molecule encoding a CHEC-7 peptide. Still another aspect of the present invention includes an isolated host cell comprising the nucleic acid molecule encoding a CHEC-7 peptide, wherein said host cell is selected from the group consisting of bacterial, fungal, mammalian, insect and plant cells. Yet another aspect of the present invention includes a host animal comprising the nucleic acid molecule encoding a CHEC-7 peptide.

Another embodiment of the present invention includes an antibody immunologically specific for an isolated CHEC-7 peptide. In one aspect, the antibody is a monoclonal antibody. In another aspect, the antibody is a polyclonal antibody.

Another embodiment of the present invention includes a kit for treating a neurodegenerative disorder or inflammatory disorder in a patient comprising a) an isolated CHEC-7 peptide; b) a pharmaceutical excipient; and optionally c) a vehicle for administration, such as a syringe or catheter, and further comprising, instructional material. In one aspect, the kit further comprises a detectable label.

Yet another embodiment of the present invention includes a kit for detecting CHEC-7 peptide comprising a) means for isolating a CHEC-7 peptide or nucleic acid encoding a CHEC-7 peptide from a biological sample; b) means for detecting and quantifying said peptides or nucleic acids; and optionally, instructional material.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2 illustrates sPLA2 activity of 8% plasma samples prepared from whole blood of healthy 57 year old male. Whole blood was incubated with 400 nM CHEC-9 (final concentration) for 2 hrs. at 4° and then samples were used to hydrolyze an sPLA2 specific substrate to give a product detected at 415 nm absorbance. The reaction was inhibited upon CHEC-9 treatment. Three enzyme reactions are shown and data is representative of that obtained from all 4 healthy volunteers. These curves, along with velocity of the reaction (Absorbance/time or milliOD/min), and several other reaction parameters are calculated by software supporting the kinetic reader. The substrate, buffer and other details of the assay are described elsewhere herein.

FIG. 10 illustrates the time course of changes in urinary sPLA2 activity following bilateral footpad immunization of DA rats with guinea pig myelin basic protein (100 µg total in CFA). Single voids from each rat were collected in metabolic cages between 9 AM and 2 PM on PI days 1 and 2 and every other day after day 2. Significant elevations in activity are found at 4-6 days PI followed by a decline. Treatment with CHEC-9 was between 2-5 PM everyday on PI days 5-15. The pattern of the sPLA2 curves in CHEC-9 and control-treated rats is somewhat similar before and after treatment. However, mean activity after 2 days of treatment was significantly attenuated by CHEC-9 (days 4 & 6 PI vs. 8 & 10 PI, $p=0.007$, **) but not after vehicle treatment ($p=0.528$ for the same period). Comparisons between groups within this period was not significant apparently because of variability in the values for individual vehicle-treated rats. Right: Western blots were prepared from pooled urine samples collected before immunization and 8 days after immunization. The urine samples were dialyzed 20 hrs. at 4° against 2 changes of 1000-fold excess of 20 mM tris-HCL, 200 µg protein loaded for immunblotting of SDS gels (reducing) using a monclonal antibody to 160 kD neurofilament protein. The blots were stripped and reacted for albumin as a loading control. The NF Ab is not cross reactive with other NF proteins or with intermediate filaments in muscle, and samples are not cross reactive with secondary antibodies. The blots suggest a post-immunization increase in a 30 kD NF (M) fragment that is most prominent in the vehicle-treated rats. A similar fragment is found in other neuropathological conditions and has been suggested to be dependent on endogenous trypsin-like enzymes (Fasani, et al., 2004). The excess in vehicle-treated rats could be the result of increased axon destruction (either central or peripheral) since we find the urinary levels of NF fragments (of different sizes) are also exaggerated in other neurodegeneration models (see below). Their appearance in normal animals could represent normal peripheral axon turnover (review by Gordon, et al., 2004). However, the origin of these fragments is unknown at present.

FIG. 11 illustrates foot edema in CHEC-9 and vehicle treated rats following bilateral foot pad immunization with myelin basic protein/CFA. The thickness of the feet was measured 10 days post immunization. CHEC-9 treatments began 5 days earlier. Measurements were made from planter to superior surface of the foot just rostral to the heel. The difference between the two groups is significant designating either rats (n=5, each condition) or feet (n=10) as the unit of observation ($p=0.008$, 0.002 respectively).

FIG. 14, comprising FIGS. 11A and 11B, shows micrographs showing the region of the conus medularis (CM) in the spinal cord of two EAE rats treated with CHEC-9 (rat #411) or vehicle (rat #410) and sacrificed 18 days after immunization. The two parasagittal sections represent nearly equivalent medio-lateral planes. There is extensive spinal cord and cellular atrophy (and/or cell infiltration) in rat 410 as well as large areas of myelin degeneration (note scale bars are equal). The clinical EAE score is shown for these two rats and consistent with the histology. Nissl-myelin stain (cyanine R followed by cresyl violet).

FIG. 16, comprising FIGS. 16A and 16B, is a series of graphs depicting urinary PLA2 enzyme activity in MS patients and controls. FIG. 16A illustrates velocities of PLA2 enzyme reactions at different substrate concentrations [S] are shown for 25 μl sample of urine from a 37 y.o. patient with stable MS, compared to an age/gender matched control. Typical hyperbolic curves were obtained for urine samples from both patients and controls, i.e., reaction velocity peaks and levels off at high [S]. Velocity is therefore proportional to the concentration of active enzyme in the urine at saturating substrate concentrations (Michaelis-Menton equation, Vmax=$K_2[E]$). Mean and s.e.m. of triplicate reactions for each concentration are shown. Inset: Western blot of 200 μg total urinary protein of 34 y.o. patient with active MS. A 14 kD sPLA2 immunoreactive band appeared (arrow) along with a 68 kD immunoreactive band of unknown identity. FIG. 16B illustrates the level of enzyme activity in MS patients with active or stable disease compared to controls, as described elsewhere herein. All measurements were made using 600 μM substrate and normalized to the average control value. There was a significant 4 and 6-fold increase in PLA2 activity compared to controls in the stable and active MS patients respectively, ($p=0.049*$; $0.0019**$, for comparison with controls).

FIG. 17, comprising FIGS. 17A and 17B, is a series of graphs depicting PLA2 activity and clinical disease in experimental autoimmune encephalomyelitis (EAE) rats treated with sPLA2 inhibitor. FIG. 17A depicts that PLA2 enzymatic activity, normalized to pre-immunization values, increased steadily to day 8 in both CHEC-9 and vehicle-treated rats. A significant reduction in activity was observed on days 10 and 12 post-immunization in the peptide treated group either by comparing values of peptide and vehicle directly ($p=0.049$, $0.026$ respectively), or by peak to trough comparison between days 8 and 12, where reduction in sPLA2 levels with peptide treatment was significant ($p=10^{-3}$) but in vehicle-treated rats was not ($p=0.491$). FIG. 17B depicts that mean clinical scores from day 10 onwards were also significantly lower in the peptide treated rats ($p<10^{-4}$).

DETAILED DESCRIPTION OF THE INVENTION

Figure 1:
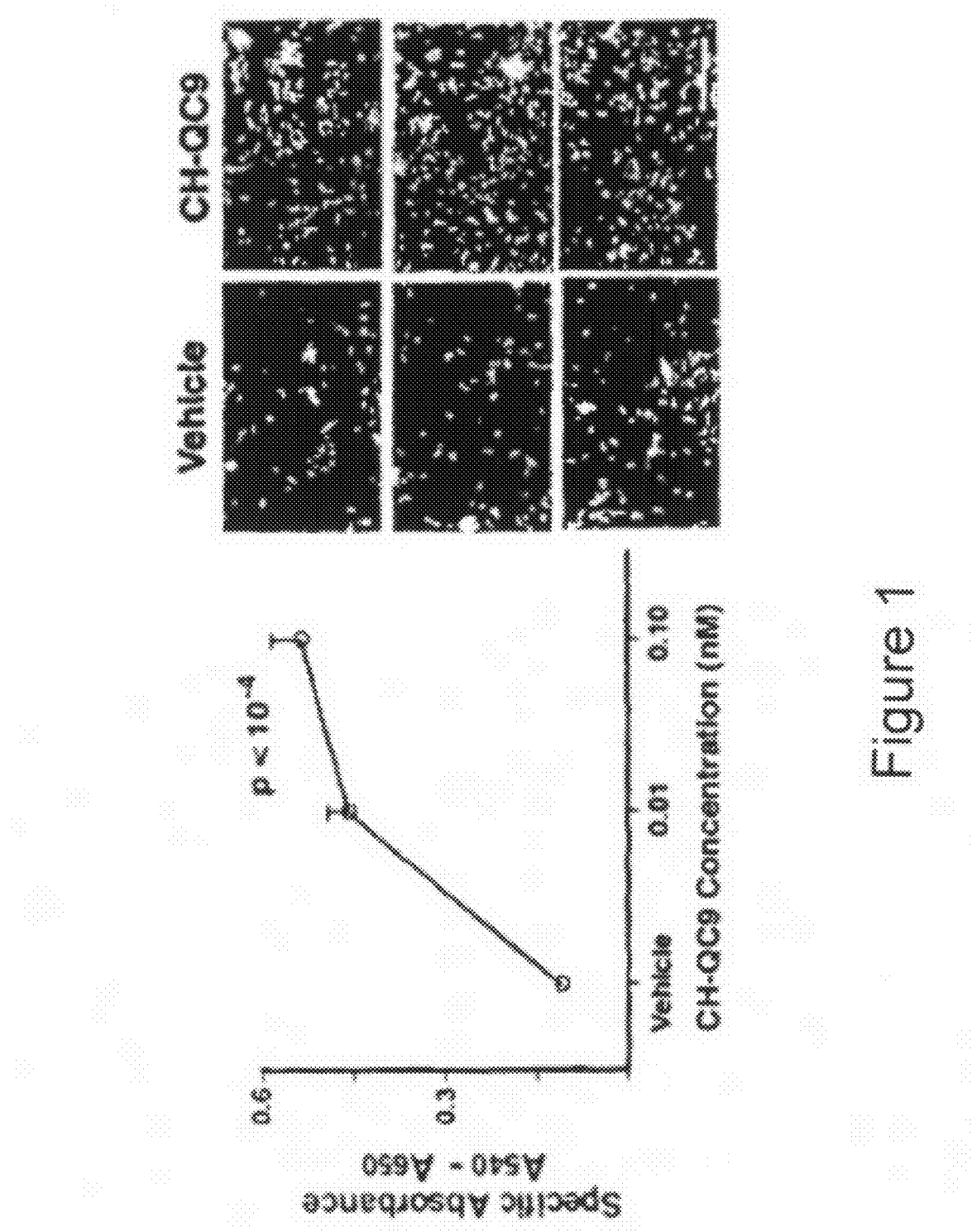
FIG. 1 shows increased survival of SY5Y neuroblastoma cells exposed to CHEC-9, following medium change and serum deprivation for 48 hrs. The cells were seeded at low density in serum and changed to serum free medium (with added CHEC-9 peptide or vehicle) after 2 hrs. Cell survival was measured with the WST electrocoupling reagent (Ocinda). The graph on the left shows increased CHEC-9 concentration correlates with increased cell survival. Three representative cultures from the 2 groups are shown in the panels on the right. Coomassie Blue stain. Bar=100 pm. (p value based on n=16 cultures for each condition in 2 separate experiments.

A nine amino acid peptide CHEASAAQC (SEQ ID NO: 1, designated CHEC-9 or CH-QC9) has been identified, synthesized and used to promote survival of neural cells in vitro and in vivo, including after cerebral cortex injury. The peptide rescues neurons that would usually shrink, die or disintegrate following traumatic brain damage. Furthermore, the peptide posses demonstrable phospholipase A2 inhibitory activity, and therefore has utility as a modulator of inflammation. A CHEC-9 peptide variant having the sequence CAHAQAESC (SEQ ID NO.: 2) also promotes survival of neural cells. A seven amino acid peptide, CHEC-7 having the sequence CHEASQC (SEQ ID NO.: 3) has also been identified which exhibits even more potent effects as a sPLA2 inhibitor than CHEC-9.

CHEC-7 and CHEC-9 constitute internal sequences of survival promoting peptide Y-P30 (U.S. Pat. No. 6,262,024). CHEC-7, CHEC-9, and Y-P30 are derived from a 12 kiloDalton (kD) endogenous human protein, DSEP (GenBank Accession #AY044239, T. J. Cunningham, et al., 2002). CHEC-9 and Y-P30 differ from the sequence of DSEP in having a cysteine at position 23, instead of lysine. Like the larger peptides, both CHEC-7 and CHEC-9 promote neuron survival and inhibit aspects of the immune response to cerebral cortex lesions, in particular the appearance and invasion of macrophages and microglia at the site of injury. Accordingly these peptides may be used for treatment of disorders involving acute neural degeneration (stroke and traumatic brain damage), as well as for treatment of several chronic neurodegenerative disorders including Alzheimer's disease and MS. In the latter applications, CHEC-7 and CHEC-9 inhibit both neuron death and the brain's immune response to degenerating elements, which should slow the progress of these disorders and attendant decline of behavioral performance. Additionally, CHEC-9 inhibits phospholipase A2, and thus may be used to treat disorders associated with inflammation.

DEFINITIONS

The articles "a" and "an" are used herein to refer to one or to more than one (i.e. to at least one) of the grammatical object of the article. By way of example, "an element" means one element or more than one element.

By the term "applicator" as the term is used herein, is meant any device including, but not limited to, a hypodermic syringe, a pipette, and the like, for administering CHEC-9 or other inhibitor of the invention to a mammal.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 75% homology.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

"Constitutive" expression is a state in which a gene product is produced in a living cell under most or all physiological conditions of the cell.

"Inducible" expression is a state in which a gene product is produced in a living cell in response to the presence of a signal in the cell.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "portion" of a polynucleotide means at least at least about fifteen to about fifty sequential nucleotide residues of the polynucleotide. It is understood that a portion of a polynucleotide may include every nucleotide residue of the polynucleotide.

By the term "specifically binds," as used herein, is meant an antibody which recognizes and binds an epitope present on a molecule, but does not substantially recognize or bind other molecules in a sample.

A "prophylactic" treatment is a treatment administered to a subject who does not exhibit signs of a disease or exhibits only early signs of the disease for the purpose of decreasing the risk of developing pathology associated with the disease.

"Preventing" a disease, as the term is used herein, means that the onset of the disease is delayed, and/or that the symptoms of the disease will be decreased in intensity and/or frequency, when an inhibitor is administered compared with the onset and/or symptoms in the absence of the inhibitor.

A "therapeutically effective amount" of a compound is that amount of compound which is sufficient to provide a beneficial effect to the subject to which the compound is administered. By way of a non-limiting example, a therapeutically effective amount of CHEC-9, for the purpose of treating MS, is an amount of CHEC-9 which is sufficient to alleviate one or more symptoms in a patient, the symptoms being associated with MS in the patient.

As used herein, the term "alleviate" refers to the lessening, decrease, or diminishing of a symptom, state, or condition. In one aspect, a symptom of a disease is alleviated when the symptom decreases in severity of occurrence or effect in a patient. In another aspect, a symptom of a disease is alleviated when the symptom is completely eradicated or eliminated from the patient.

As used herein, the term "treat" or "treating" refers to alleviating one or more symptoms of a disease or disorder in a mammal.

As used herein, the term "degeneration of a neuron" refers to any decrease in activity, viability, or function of a neuron from the normal healthy state of the neuron. In one aspect, degeneration of a neuron refers to a minor decrease in activity, viability, or function of a neuron from the normal healthy state of the neuron. In another aspect, degeneration of a neuron refers to the complete incapacitation of the neuron such that the neuron cannot function in any capacity, and even death of the neuron. The term "degeneration of axon" similarly refers to the activity, viability or function of an axon.

As used herein, the term "detecting an increase" of a protein, compound or activity refers to the measurement of a level of protein, compound or activity, wherein the measurement reflects a value higher than the value obtained from an identical measurement under a healthy, non-diseased condition in a subject. By way of a non-limiting example, a measurable increase in the activity of PLA2 in the urine of a subject with MS is one way to "detect an increase" in PLA2 activity, wherein the increase is compared to the level of PLA2 activity in the urine of the subject without MS. The skilled artisan will understand that the level of activity of PLA2 in the urine of a subject having MS, for example, can be standardized against the level of PLA2 activity in a separate, healthy patient, in order to "detect an increase" in the urine PLA2 activity in the patient afflicted with MS.

As used herein, the term "at least a fragment" refers to a polypeptide comprising at least two consecutive amino acid residues, wherein the consecutive amino acid residues correspond to the sequence of a larger peptide or protein. By way of a non-limiting example, the dipeptide Ser-Arg is a fragment of a larger polypeptide containing the sequence Ser-Arg within the overall polypeptide. Similarly, the dipeptide Ser-Arg is a fragment of a larger polypeptide consisting of the sequence Ser-Arg-Gly. That is, a polypeptide lacking even one amino acid residue is "at least a fragment" of the larger, complete polypeptide.

An "autoimmune disease," as used herein, is a disease which occurs when one or more components of the immune system targets the cells, tissues, and/or organs of a person's own body. Autoimmune diseases include, but are not limited to Multiple sclerosis, Myasthenia gravis, Autoimmune neuropathies such as Guillain-Barré, Autoimmune uveitis, Inflammatory Bowel Disease (including Crohn's Disease and Ulcerative colitis) Primary biliary cirrhosis, Autoimmune hepatitis, Type 1 or immune-mediated diabetes mellitus, Autoimmune thyroid disease (including Grave's Disease and Hashimoto's thyroiditis), Autoimmune oophoritis and orchitis, Autoimmune disease of the adrenal gland, Autoimmune hemolytic anemia, Pernicious anemia, Autoimmune thrombocytopenia, Temporal arteritis, Antiphospholipid syndrome, Vasculitides such as Wegener's granulomatosis, Behcet's disease, Rheumatoid arthritis, Systemic lupus erythematosus, Scleroderma, Polymyositis, dermatomyositis, Spondyloarthropathies such as ankylosing spondylitis, Sjogren's syndrome, Psoriasis, Dermatitis herpetiformis, Pemphigus vulgaris, and Vitiligo.

I. Compositions

A "CHEC-9 peptide" is a peptide having the sequence of CHEASAAQC (SEQ ID NO: 1). The peptide may be linear or cyclic. The term "CHEC-9 peptide" includes variants of SEQ ID NO:1, wherein as few as 1 or as many as 9 amino acids are changed, provided that the peptide still promotes neuron survival, inhibits a brain's immune response to degenerating elements, and/or inhibits phospholipase A2. Variants may have mutations comprising insertions, deletions, or substitutions of amino acids. Variants preferably comprise conservative amino acid substitutions.

A "CHEC-7 peptide" is a peptide having the sequence CHEASQC (SEQ ID NO.: 3). The peptide may be linear or cyclic. The term "CHEC-7 peptide" may include variants of SEQ ID NO: 3, wherein as few as 1 or as many as 7 amino acids are changed, provided that the peptide still promotes neuron survival, inhibits a brain's immune response to degenerating elements, and/or inhibits phospholipase A2. Variants may have mutations comprising insertions, deletions, or substitutions of amino acids. Variants preferably comprise conservative amino acid substitutions.

A "conservative amino acid substitution" as defined herein refers to replacement of an amino acid with a functionally and biochemically equivalent amino acid. These substitutions provide similar or enhanced function of a peptide. Functionally-equivalent amino acids are amino acids which share a common structure, side chain, polarity, and so forth. Examples of amino acids which may be functionally equivalent are:

| | |
|---|---|
| hydrophobic | Ala, His, Ile, Leu, Met, Phe, Trp, Tyr, Val |
| neutral hydrophilic | Cys, Ser, Thr |
| polar | Asn, Gln, Ser, Thr |
| acidic/negatively charged | Asp, Glu |
| charged | Arg, Asp, Glu, His, Lys |
| basic/positively charged | Arg, His, Lys |
| basic | Arg, Asn, Gln, His, Lys |
| residues that influence chain orientation | Gly, Pro |
| aromatic | His, Phe, Trp, Tyr |

Nucleic Acid Molecules

One embodiment of the present invention encompasses nucleic acid molecules encoding a CHEC-9 peptide. Nucleic acid molecules encoding a CHEC-9 peptide may be prepared by two general methods: (1) synthesis from appropriate nucleotide triphosphates, or (2) isolation from biological sources. Both methods utilize protocols well known in the art. Preparation of an isolated nucleic acid molecule of the invention may be by oligonucleotide synthesis. The nucleic acid synthesized may be any combination of codons which encode CHEC-9 peptide. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Alternatively, nucleic acid sequences encoding a CHEC-9 peptide may be isolated from appropriate biological sources using methods known in the art. Suitable probes for this purpose are derived from sequences which encode the amino acids of CHEC-9.

In another embodiment, nucleic acids encoding CHEC-7 may be prepared as described in detail for CHEC-9 nucleic acids elsewhere herein. In yet another embodiment, nucleic acids encoding CHEC-7 may be prepared, isolated and purified using methods and protocols well known in the art. Alternatively, nucleic acid sequences encoding a CHEC-7 peptide may be isolated from appropriate biological sources using methods known in the art. Suitable probes for this purpose are derived from sequences which encode the amino acids of CHEC-7.

In accordance with the present invention, nucleic acids having the appropriate level of sequence homology with a CHEC-9 peptide may be identified by using hybridization and washing conditions of appropriate stringency. In another embodiment, nucleic acids having the appropriate level of sequence homology with a CHEC-7 peptide may be identified by using hybridization and washing conditions of appropriate stringency. For example, hybridizations may be performed, according to the method of Sambrook et al., Molecular Cloning, Cold Spring Harbor Laboratory (1989), using a hybridization solution comprising: 5×SSC, 5×Denhardt's reagent, 1.0% SDS, 100 pg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% 5 SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology (Sambrook et al., 1989) is as follows:

$$T_t = 81.5° C. + 16.6 \log [Na^+] + 0.41 (\% G+C) - 0.63 (\% \text{formamide}) - 600/\#bp \text{ in duplex}$$

As an illustration of the above formula, using $[Na^+]=[0.3681$ and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1× SSC and 0.5% SDS at 65° C. for 15 minutes.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable E. coli host cell.

CHEC-9-encoding nucleic acid molecules of the invention include cDNA, genomic DNA, RNA, and fragments thereof which may be single- or double-stranded. In another embodiment, CHEC-7 encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention. As mentioned previously, such oligonucleotides are useful as probes for detecting or isolating CHEC-9 related nucleic acids. In another embodiment, such oligonucleotides are useful as probes for detecting or isolating CHEC-7 related nucleic acids.

It will be appreciated by persons skilled in the art that variants (e.g., allelic variants) of a CHEC-9 or a CHEC-7 sequence exist in the human population, and must be taken into account when designing and/or utilizing oligonucleotides of the invention. Accordingly, it is within the scope of the present invention to encompass such variants, or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants.

Additionally, the term "substantially complementary" refers to oligonucleotide sequences that may not be perfectly matched to a target sequence, but such mismatches do not materially affect the ability of the oligonucleotide to hybridize with its target sequence under the conditions described.

Proteins

CHEC-7 and CHEC-9 peptides, and functional variants thereof may be prepared in a variety of ways, according to known methods. The peptide may be synthesized using an automated peptide synthesizer. Alternatively, the peptide may be purified from appropriate sources, e.g., transformed bacterial or animal cultured cells or tissues, by immunoaffinity purification. The availability of nucleic acid molecules encoding CHEC-9 peptide enables production of the peptide using in vitro expression methods known in the art. For example, a CHEC-9 encoding polynucleotide may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or Gibco-BRL, Gaithersburg, Md. In other embodiments, a CHEC-7 encoding polynucleotide may be cloned into an appropriate in vitro transcription vector for in vitro transcription, followed by cell-free translation in a suitable cell-free translation system. In still another embodiment, an in vitro expression vector can be engineered to express both CHEC-7 and CHEC-9 peptides, or variants thereof. For example, a member of the pTrident vector family, a multicistronic expression vector, is engineered for the simultaneous and coordinated expression of multiple independent genes in mammalian cells using a single promoter.

Alternatively, larger quantities of peptides may be produced by expression in a suitable prokaryotic or eukaryotic system. For example, part or all of a DNA molecule, such as a nucleic acid encoding CHEC-9 may be inserted into a plasmid vector adapted for expression in a bacterial cell, such as *E. coli.* In another embodiment, a nucleic acid encoding CHEC-7, or a fragment or variant thereof, may be inserted into a plasmid vector adapted for expression in a bacterial cell. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

A peptide produced by gene expression in a recombinant prokaryotic or eukaryotic system may be purified according to methods known in the art. In a preferred embodiment, a commercially available expression/secretion system can be used, whereby the recombinant peptide/protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

The human CHEC-9 peptide and functional homologs or variants thereof, prepared by the aforementioned methods, may be analyzed according to standard procedures. For example, such proteins may be subjected to amino acid sequence analysis, according to known methods. One such peptide variant which also has neuron protective activity is the peptide having the sequence CAHAQAESC. The CHEC-9 peptide may be oxidized (cyclized), or alkylated (linearized).

In another embodiment, the CHEC-7 peptide and a functional homolog or variant thereof, prepared by the aforementioned methods, may be analyzed according to standard procedures. For example, such proteins may be subjected to amino acid sequence analysis, according to known methods. The CHEC-7 peptide may be oxidized (cyclized), or alkylated (linearized).

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Antibodies

The present invention also provides antibodies capable of immunospecifically binding to peptides of the invention. In one embodiment, polyclonal antibodies directed toward CHEC-9 peptide, or any variant thereof, may be prepared according to standard methods. In another embodiment, polyclonal antibodies directed toward CHEC-7 peptide, or any variant thereof, may be prepared according to methods known in the art. In yet another embodiment, monoclonal antibodies are prepared, which react immunospecifically with CHEC-9 peptide. In still another embodiment, a monoclonal antibody is prepared which binds specifically to CHEC-7.

Polyclonal and/or monoclonal antibodies may be prepared as described in several laboratory protocol handbooks, and scholarly journals including: Kohler and Milstein, Nature, 256: 495-7 (1975); Molecular Cloning: A Laboratory Manual, Sambrook et al. eds., Cold Spring Harbor Laboratory Press (1989); Ausubel et al. (supra), and Antibodies: A Laboratory Manual, Harlow and Lane eds., Cold Spring Harbor Laboratory Press (1988).

Polyclonal or monoclonal antibodies that immunospecifically interact with a CHEC-9 peptide may be utilized for identifying and purifying a peptide. In another embodiment, polyclonal or monoclonal antibodies that immunospecifically interact with a CHEC-7 peptide may be utilized for identifying and purifying a peptide. For example, antibodies may be utilized for affinity separation of peptides with which they immunospecifically interact. Antibodies may also be used to immunoprecipitate peptides from a sample containing a mixture of peptides/proteins and other biological molecules. Other uses of antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, C1 and CHI domains; the Fd fragment consisting of the VH and CHI domains; the Fv fragment consisting of the VL and VH domains of a single arm of an antibody; the dAb fragment which consists of a VH domain; isolated CDR regions and F (ab') 2 fragments, a bivalent fragment including two Fab fragments linked by a disulphide bridge at the hinge region. Single chain Fv fragments are also included.

II. Uses of CHEC-7 and CHEC-9-Encoding Nucleic Acids CHEC-7 and CHEC-9 Proteins and Antibodies Thereto The method of the invention can be applied to patients with, and animal models of, neurodegenerative diseases including of Multiple Sclerosis, Amyotrophic Lateral Sclerosis, Alzheimer's disease, spinal cord injury, and brain damage, among others. As will be understood by the skilled artisan when armed with the present disclosure, the invention is also applicable to the characterization of other inflammation-related conditions in a subject. With the subjects, the urinary measurements can be correlated with the standard performance scales used to measure severity of the nervous system disorder. For the animals, standardized behavioral testing methods can be used.

In another embodiment of the invention, a very stable peptide inhibitor of secreted phospholipase A2 (sPLA2) that is effective for systemic treatment of neurodegeneration associated with inflammation has been discovered. The peptide—called CHEC-7—inhibits aspects of the inflammatory cascade that follow damage to the CNS, and as a result, rescues neurons that would usually degenerate. Multiple Sclerosis is characterized by recurring CNS inflammation, axonal and cell degeneration, and subsequent appearance of neurological deficits. After repeated recurrences, the patients are often chronically disabled. Based on the remarkable properties of CHEC-9 and CHEC-7, and on recent reports concerning the role of sPLA2 activity in MS models, the invention set forth herein demonstrates that CHEC-9 and CHEC-7 can be used as therapy for Multiple Sclerosis. The invention also demonstrates preclinical testing of CHEC-9, including an ex vivo patient component, in order to demonstrate the feasibility of development of the CHEC-9 peptide as a pharmaceutical.

Therefore, in an embodiment, the present invention provides a method of treating MS in a patient having MS. In one aspect, the method includes administering to a patient having MS a CHEC-9 peptide. In another aspect, the method includes administering to a patient having MS a CHEC-7 peptide. Methods of administration of a peptide will be understood by the skilled artisan when armed with the disclosure set forth herein. Such methods are also described in detail elsewhere herein.

In an aspect of the invention, CHEC-9 may be used as an anti-inflammatory or cell survival agent for a variety of disorders. This is because CHEC-9 is an uncompetitive sPLA2 inhibitor, as demonstrated herein. The advantage of an uncompetitive sPLA2 inhibitor for enzyme inhibition therapy is that, unlike competitive inhibitors, uncompetitive inhibitors are not rendered ineffective by the accumulation of unmodified substrate. Such conditions apply to several instances of neuroinflammation where there are cascading increases in sPLA2s and their substrates, both systemically and in the CNS.

In another aspect of the invention, CHEC-7 may be used as an anti-inflammatory or cell survival agent for a variety of disorders.

It will also be understood, based on the disclosure set forth herein, that a CHEC-9-like peptide may also be useful according to the methods of the present invention as set forth herein. This is because the present invention teaches the structure and properties of a peptide—namely, CHEC-9—that is useful for detecting inflammatory conditions and treating such conditions, among other things.

Further, it will also be understood, based on the disclosure set forth herein, that a CHEC-7-like peptide may also be useful according to the methods of the present invention as set forth herein. This is because the present invention teaches the structure and properties of a peptide—namely, CHEC-7—that is useful for detecting inflammatory conditions and treating such conditions, among other things.

Nucleic Acids

CHEC-9-encoding nucleic acids may be used for a variety of purposes in accordance with the present invention. CHEC-9-encoding DNA, RNA, or fragments thereof may be used as probes to detect the presence of and/or expression of nucleic acids encoding a peptide of interest. In another embodiment, CHEC-7-encoding nucleic acids may be used for a variety of purposes in accordance with the present invention. CHEC-7-encoding DNA, RNA, or fragments thereof may be used as probes to detect the presence of and/or expression of nucleic acids encoding a peptide of interest. Methods in which nucleic acids may be utilized as probes for such assays include, but are not limited to: (1) in situ hybridization; (2) Southern hybridization (3) northern hybridization; and (4) assorted amplification reactions such as polymerase chain reactions (PCR). Thus, CHEC-9-encoding nucleic acids of the present invention may be used for detecting CHEC-9 in vitro or in vivo. In another embodiment, CHEC-7 encoding nucleic acids may be used to detect CHEC-7 in vitro or in vivo.

Additionally, the nucleic acids of the invention may be used to identify genes encoding proteins that interact with CHEC-9 peptides (e.g., by the "interaction trap" technique).

In another embodiment, the nucleic acids of the invention may be used to identify genes encoding proteins that interact with CHEC-7 peptides The CHEC-9 nucleic acids of the invention may be introduced into host cells. In a preferred embodiment, mammalian cell lines are provided which comprise a CHEC-9-encoding nucleic acid or a variant thereof. In another embodiment, CHEC-7 encoding nucleic acids of the invention may be introduced into host cells. In yet another embodiment, mammalian cell lines are provided which comprise a CHEC-7-encoding nucleic acid or a variant thereof. Host cells contemplated for use include, but are not limited to NIH3T3, CHO, HELA, yeast, bacteria, insect and plant cells. The encoding nucleic acids may be operably linked to appropriate regulatory expression elements suitable for the particular host cell to be utilized. Methods for introducing nucleic acids into host cells are well known in the art. Such methods include, but are not limited to, transfection, transformation, calcium phosphate precipitation, electroporation and lipofection.

The host cells described above may be used as screening tools to identify compounds that modulate CHEC-9 expression and/or activity. Modulation of CHEC-9 expression and/or activity maybe assessed by measuring alterations in CHEC-9 mRNA or peptide levels in the presence of the test compound. In yet other embodiments, the host cells may be used as screening tools to identify compounds that modulate CHEC-7 expression and/or activity.

As described above, CHEC-9-encoding nucleic acids are also used to produce large quantities of substantially pure CHEC-9 peptides, or selected portions thereof. In another embodiment of the invention, CHEC-7-encoding nucleic acids are also used to produce large quantities of substantially pure CHEC-7 peptides, fragments, homologues, variants or selected portions thereof.

CHEC-7 and CHEC-9 Peptides

It has been discovered that CHEC-9 promotes survival of neural cells in vitro and in vivo, and inhibits phospholipase A2. Thus, peptide CHEC-9 and pharmaceutical preparations comprising the same have broad utility in the treatment of neuron damage, neurodegenerative disease, and disorders with an inflammatory component.

The present specification discloses for the first time that CHEC-7 is a potent inhibitor of phospholipase A2. In an aspect of the invention, a CHEC-7 peptide is a more potent inhibitor of phospholipase A2 than is CHEC-9. Thus, CHEC-7 peptide and pharmaceutical preparations comprising the same have broad utility in the treatment of neuron damage, neurodegenerative disease, and disorders with an inflammatory component. The uses of these materials described herein below are intended to exemplify their utility, and are not intended to limit the invention.

Such neurodegenerative diseases and disorders include, but are not limited to (1) trauma, (2) stroke, (3) nonspecific anoxia (i.e., anoxia due to drowning, suffocation, etc.), (4) neurodegenerative diseases such as Multiple Sclerosis, Alzheimer's disease, Parkinson's disease and amyotrophic lateral sclerosis (ALS); and (5) mental retardation syndromes associated with progressive neuronal degeneration (e-g., cerebral palsies).

Disorders with an inflammatory component include, but are not limited to, (1) asthma; (2) autoimmune disorders; (3) allergies; (4) arthritis; and (5) any disorder which might benefit from treatment using a steroid or a phospholipase A2 inhibitor.

Antibodies

Purified CHEC-9 peptide, or fragments thereof, may be used to produce polyclonal or monoclonal antibodies which also may serve as sensitive detection reagents for the presence and accumulation of CHEC-9 peptide (or complexes containing CHEC-9 peptide) in mammalian cells or body fluids. Recombinant techniques enable expression of fusion proteins containing part or all of CHEC-9 peptide. The peptide may be used to advantage to generate an array of monoclonal antibodies specific for CHEC-9, thereby providing even greater sensitivity for detection of CHEC-9 in cells or body fluids. In another embodiment, purified CHEC-7 peptide, or fragments thereof, may be used to produce polyclonal or monoclonal antibodies which also may serve as sensitive detection reagents for the presence and accumulation of CHEC-7 peptide (or complexes containing CHEC-7 peptide) in mammalian cells or body fluids. Recombinant techniques enable expression of fusion proteins containing part or all of CHEC-7 peptide. The peptide may be used to advantage to generate an array of monoclonal antibodies specific for CHEC-7, thereby providing even greater sensitivity for detection of CHEC-7 in cells or body fluids.

Polyclonal or monoclonal antibodies immunologically specific for CHEC-9 peptide may be used in a variety of assays designed to detect and quantitate the peptide. Such assays include, but are not limited to: (1) flow cytometric analysis; (2) immunochemical detection/localization of CHEC-9 peptide; and (3) immunoblot analysis (e.g., dot blot, Western blot) of extracts from various cells. Additionally, as described above, anti-CHEC-9 antibodies can be used for purification of CHEC-9 peptide and any associated subunits (e.g., affinity column purification, immunoprecipitation). In another embodiment, monoclonal or polyclonal antibodies immunologically specific for CHEC-7 peptide may be used to detect and quantitate the peptide in a variety of assays including but not limited to (1) flow cytometric analysis; (2) immunochemical detection/localization of CHEC-7 peptide; and (3) immunoblot analysis (e.g., dot blot, Western blot) of extracts from various cells. Additionally, as described above, anti-CHEC-7 antibodies can be used for purification of CHEC-7 peptide and any associated subunits (e.g., affinity column purification, immunoprecipitation).

Pharmaceutical Compositions and Therapies

A pharmaceutical preparation of CHEC-9 is formulated for administration to patients by combining the peptide with a biologically acceptable medium, such as water, buffered saline, or osmotically-adjusted media such as polyol (e.g., glycerol, propylene glycol, liquid polyethylene glycol and the like) or suitable mixtures thereof. A pharmaceutical preparation of CHEC-7 is formulated for administration to patients by combining the peptide with a biologically acceptable medium, such as water, buffered saline, or osmotically-adjusted media such as polyol (e.g., glycerol, propylene glycol, liquid polyethylene glycol and the like) or suitable mixtures thereof. The term "biologically acceptable medium" includes all solvents, dispersion media and similar components which may be appropriate for the selected route of administration of the pharmaceutical preparation. The use of such biologically acceptable media for pharmaceutical preparations is well known in the art. Unless a conventional medium or agent is incompatible with the active ingredient of CHEC-7 or CHEC-9, its use in the pharmaceutical preparation of the invention is contemplated.

The pharmaceutical preparation is preferably administered parenterally, by introduction into the central nervous system of the patient. This may be accomplished by intracerebroventricular infusion targeted to the location of neuron damage. Other methods, such as systemic administration via an i.v. may also be utilized to administer a pharmaceutical preparation containing. Administration may be by any method that allows CHEC-7 or CHEC-9 to cross the blood/brain barrier, either alone or linked to a carrier, including injection into the bloodstream, subcutaneous or intramuscular injection, as well as oral, intranasal, rectal and ophthalmic administration. In still another embodiment, solutions comprising CHEC-7 or CHEC-9 may be injected subcutaneously.

CHEC-9 peptide may be administered topically or transdermally, such as in a cream, salve, spray, ointment, or dermal patch. In a preferred embodiment, CHEC-7 peptide may also be administered topically or transdermally, such as in a cream, salve, spray, ointment, or dermal patch Alternatively, CHEC-7 peptides, CHEC-9 peptides, or a combination thereof, are incorporated into a solid matrix, which can be implanted into regions of the nervous system/brain requiring treatment. For example, a pre-determined concentration of CHEC-9 may be mixed in equal parts with a 2% sodium alginate medium, and entrapped in the resulting gel matrix. The sodium alginate gel is polymerized in the form of small beads by dropping the gel into a 0.5 M $CaCl_2$ solution. Other solid or semi-solid biologically compatible matrices are also contemplated for use in the present invention. These include various natural bio-polymers, such as xanthan and carob gums (See Mugnier et al., Appl. Environ. Microbial., 50: 108-14 (1985).

The pharmaceutical preparation comprising the active ingredient is advantageously formulated in dosage units, which is defined herein as a discrete unit of the pharmaceutical preparation appropriate for the patient undergoing treatment. As used herein, the term "patient" refers to humans and animals. A dosage will contain the quantity of active ingredient determined to produce the desired therapeutic effect in conjunction with the selected pharmaceutical carrier.

The appropriate dosage of a pharmaceutical preparation comprising CHEC-7, CHEC-9, or a combination thereof, as the active ingredient may be determined by in vitro and in vivo procedures. The optimum effective concentration of CHEC-7, CHEC-9, or a combination thereof, is dependent upon the type of neuron being treated and the protocol and source used for purification. Therefore, once the target neuron population has been identified, the optimum effective concentration of therapeutic molecule according to the present invention may be determined by an in vitro assay.

By way of a non-limiting example, a selected neuron population may be grown in culture for 2-4 days in defined serum-free medium. Pre-determined concentrations of CHEC-9 in an appropriate biological medium are then added to the culture dishes every 24 hours. After the incubation period, neurons and dendrites may be identified by immunocytochemically, e.g., with an antibody against a neuron-specific marker, such as MAP2. Neuron survival and neurite outgrowth is then determined. By comparing the effect of each concentration of CHEC-9 on neurite outgrowth and neuron survival, an optimum concentration for the specific neuron population is determined.

After the optimum in vitro concentration of CHEC-7, CHEC-9, or a combination thereof, has been determined for a specific neuron population, an appropriate dosage may be deduced by an in vivo assay on laboratory animals, such as rats. An equivalent lesion in a primate or human would damage approximately 15-fold more cortical tissue. The area of brain damage is determined by standard imaging techniques, e.g., MRI. Therefore, that lesion cavity must be treated with an approximately 15-fold greater amount of the factor.

CHEC-9 may be administered in any effective dosage amount determined as set forth above. An exemplary dose is a subcutaneous administration of 50-500 µg/kg of CHEC-9 peptide. This dose may be administered immediately after, within 1 hour, 2 hours, 12 hours, or 1 day of acute injury, or periodically in the case of a chronic condition. In another embodiment, CHEC-7 may be administered in any effective dosage amount determined as set forth above. In yet another embodiment, a combination of CHEC-7 and CHEC-9 may be administered in an effective dosage amount determined as set forth above.

A pharmaceutical preparation containing CHEC-7, CHEC-9, or a combination thereof, may be administered as a one-time dosage for cases of acute anoxia or trauma, or it may be administered at appropriate intervals in the case of chronic degenerative disease, until the symptoms of the disease are reduced or eliminated. The appropriate interval of administration of the pharmaceutical preparation will depend on the type of neuron damage being treated and the condition of the patient.

CHEC-7, CHEC-9, or a combination thereof, may be administered in linear or cyclized form. Additionally, CHEC-7, CHEC-9, or a combination thereof, may be administered in combination with another therapeutic agent, such as a steroid, a non-steroidal anti-inflammatory drug (NSAID; e.g. Ibuprofen, Naproxen, Ketoprofen), Interferon beta-1b (e.g. Betaseron), Interferon beta-1a (Avonex), high dose and frequency interferon beta-1a (Rebif), Glatiramer (Copaxone), Mitoxantrone (Novantrone), Corticosteroids (methylprednisolone, prednisone, dexamethasone), muscle relaxants (Baclofen, Dantrolene, Tizanidine, Cyclobenzaprine, Clonazepam, Diazepam), anticholinergics (Propantheline, Tolterodine Dicyclomine), urinary tract antispasmodics, (Oxybutynin), tricyclic antidepressants (Amitriptyline, Imipramine), antidiuretic hormone (Desmopressin, DDAVP), anticonvulsants (Carbamazepine, Phenyloin, Acetazolamide, Lamotrigine), cntral nervous system stimulants (Pemoline), Selective Serotonin Reuptake Inhibitors (SSRIs; Citalopram, Fluoxetine, Paroxetine, Sertraline), Phosphodiesterase-5 Inhibitors (Sildenafil, Tadalafil, Vardenafil), among others.

Kits for Performing the Disclosed Methods

In one broad aspect, the present invention encompasses kits for use in administering CHEC-9. Such a kit may comprise a CHEC-9 peptide in a pharmaceutically acceptable excipient, such as artificial cerebral spinal fluid. The kit may also comprise devices which facilitate administration of the peptide, such as catheters and syringes.

In another aspect, the present invention encompasses kits for use in administering CHEC-7. Such a kit may comprise a CHEC-7 peptide in a pharmaceutically acceptable excipient, such as artificial cerebral spinal fluid. The kit may also comprise devices which facilitate administration of the peptide, such as catheters and syringes.

In yet another aspect, the present invention encompasses kits for use in administering CHEC-7 and CHEC-9. Such a kit may comprise a CHEC-7 peptide and a CHEC-9 peptide in a pharmaceutically acceptable excipient, such as artificial cerebral spinal fluid. The kit may also comprise devices which facilitate administration of the peptide, such as catheters and syringes.

In still another aspect, the present invention encompasses kits for use in administering CHEC-7, CHEC-9, or a combination thereof, in combination with another therapeutic agent, such as an anti-inflammatory agent, such as a steroid, a non-steroidal anti-inflammatory drug (NSAID), as well as combination therapies, and the like.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed herein are now described.

Example 1

Survival of Neural Cells is Supported by CHEC-9

A thirty amino acid N-terminal fragment of DSEP called Y-P30, was originally purified from the culture medium of neural cell lines exposed to hydrogen peroxide. Y-P30 promotes neuron survival and inhibits the appearance and differentiation of monocyte derivatives (macrophages/microglia) in vitro and in vivo, including after systemic administration (Cunningham, T J et al., 1998, J. Neurosci. 18:7047-7060; Cunningham, T. J., et al., 2000, Exp. Neurol. 163:457-468). The cDNA and the gene location for full length human DSEP have been identified and encode a 12 kD secreted polypeptide. When the full-length human protein is expressed in either mouse or human neural cells, these cells become resistant to a variety of toxic treatments, including immune cell attack in xenocultures and in vivo (Cunningham T J, et al., in press). Based on the Y-P30 experiments, it was concluded that the survival and immune evasion activities of DSEP could be accomplished for the most part by the N terminal amino acids. However, the sequence of the secreted form of the native peptide differs from Y-P30 in that the latter was made with cysteines at both positions 15 and 23 while the native molecule contains only one cysteine at position 15 (with a lysine at position 23). In ongoing studies of biologically active forms of Y-P30, it was found that crosslinking the cysteines confers greater survival-promoting activity in vitro than a similar 30 amino acid fragment made without the K to C substitution, or a scrambled peptide where the amino acids (including those between the two cysteines) were out of order. The K to C substitution therefore stabilizes an active conformation of DSEP by allowing the formation of an intramolecular disulphide bond. Therefore this part of the Y-P30 sequence—CHEASAAQC, designated herein as CHEC-9, was tested for DSEP/Y-P30-like activity.

Among other things, the present invention demonstrates that 1) Inhibition of systemic sPLA2 activity by injection of CHEC-9 will inhibit the progression of neurological symptoms and suppress the cellular immune response in rodent MS models; and that 2) sPLA2 activity is elevated in the blood and urine of patients with relapsing/remitting Multiple Sclerosis during active disease. CHEC-9 will inhibit this increased activity.

To this end, CHEC-9 and control treatment schedules are applied to Dark Agouti rats immunized with 1) myelin basic protein (moderate EAE) or 2) spinal cord homogenate (severe EAE). The rats are monitored daily for blood and urine sPLA2 activities and the development of EAE symptoms. Maximum levels of clinical disease are recorded and correlated with myelin/axonal degeneration, perivascular infiltrates, and immune cells including macrophages/microglia, granulocytes (neutrophils), and T-cells.

Additionally, the progress of the inflammatory response in rats with severe EAE is monitored with CHEC-9 and control treatment. This analysis includes quantification of the numbers and time course of appearance of degenerating axons and different inflammatory cells, as well as blood and tissue levels/activity of sPLA2, Thromboxane A2, Leukotriene B4 and Prostaglandin E2, and a panel of cytokines in multiplex assay system. The arachidonic acid metabolites (TBXA2, LTB4, PGE2) and many of the cytokines that are measured are known to be co-regulated in conditions of inflammation. These experiments therefore demonstrate the effects of CHEC-9 on the appearance and levels of downstream proinflammatory agents directed by arachidonic acid metabolism, as a further impetus for clinical development of this peptide.

In another embodiment, sPLA2 activity is measured in plasma and urine samples from patients with relapsing/remitting Multiple Sclerosis and compared to samples from healthy controls. The patient population can include individuals in both active and static disease states and include MS patients not on treatment studied at baseline, as well as those in defined treatment paradigms. EDSS and MSFC disability scores are measured for comparison with sPLA2 levels. A fraction of each blood sample is incubated with CHEC-9 to determine if the peptide inhibits sPLA2 activity in MS (as it does after treatment of whole blood of healthy volunteers). Downstream AA metabolites and multiple cytokines are measured in the plasma samples with and without prior CHEC-9 treatment.

Synthesis of Peptides

Peptide synthesis was performed at the Protein Chemistry Laboratory in the Department of Pathology and Laboratory Medicine University of Pennsylvania. The peptides were HPLC purified on a C18 column, dried, reconstituted in water and dried again. Peptide stock solutions (200-250 pg/ml, 218-273 pM) were prepared in 50 mM tris pH=7.4 or DMEM and incubated at room temperature overnight or for 2 hrs at 370. Free sulphydryls were measured using Ellman's reagent (DTNB, 20 0.04 mg/ml) in 0.1 M NaH2P04, 20 mM EDTA, pH=8 by mixing pl sample with 275 pl reaction buffer. Absorbance of these samples was measured at 450 nm with a 808-xl microplate reader (Biotek Instruments), and was at background levels after cross-linking. In addition, the formation of intramolecular disulphide bond in selected samples was verified by determining the exact molecular mass of the unfolded versus folded peptides using electrospray mass spectrometry (LC-ZQ Mass Spectrometer, Waters).

CHEC-9 Protects Neural Cells Subjected to Stress In Vitro

Various concentrations of CHEC-9 were tested in a stress test consisting of medium change followed by serum deprivation (see Cunningham, et al., 2000, Exp. Neurol. 163:457-468; Cunningham et al., 2002, Exp. Neurol. 177:32-39). The CHEC-9 molecule was found to rescue cells when used at concentrations of 0.1 and 0.01 pM (10-100 picomolar). Optimal activity of the peptide was achieved after pre-incubation (2501~1 with 10 mM adenosine triphosphate (Na-ATP) in a reaction mixture containing 120 mM KCl, 1 mM CaCl2, 25 mM NaCl, and 25 mM tris (pH=7.4). This mixture was diluted in culture medium and then added to the stressed cells at the appropriate active picomolar concentrations. Vehicle treatment consisted of incubation buffer without the peptide at the appropriate dilutions. Cell survival is measured by either counting surviving attached cells or, as shown in FIG. 1, by colormetric determination after applying an electrocoupling reagent that responds to chemical reactions in normal cellular respiration. The number of neurons protected in the cultures is estimated to be between 3 and 10 fold, depending on the length of serum deprivation and the starting concentration of cells.

CHEC-9 Protects Cerebral Cortex Neurons after Cortical Stab Wounds in Rats

Figure 2:
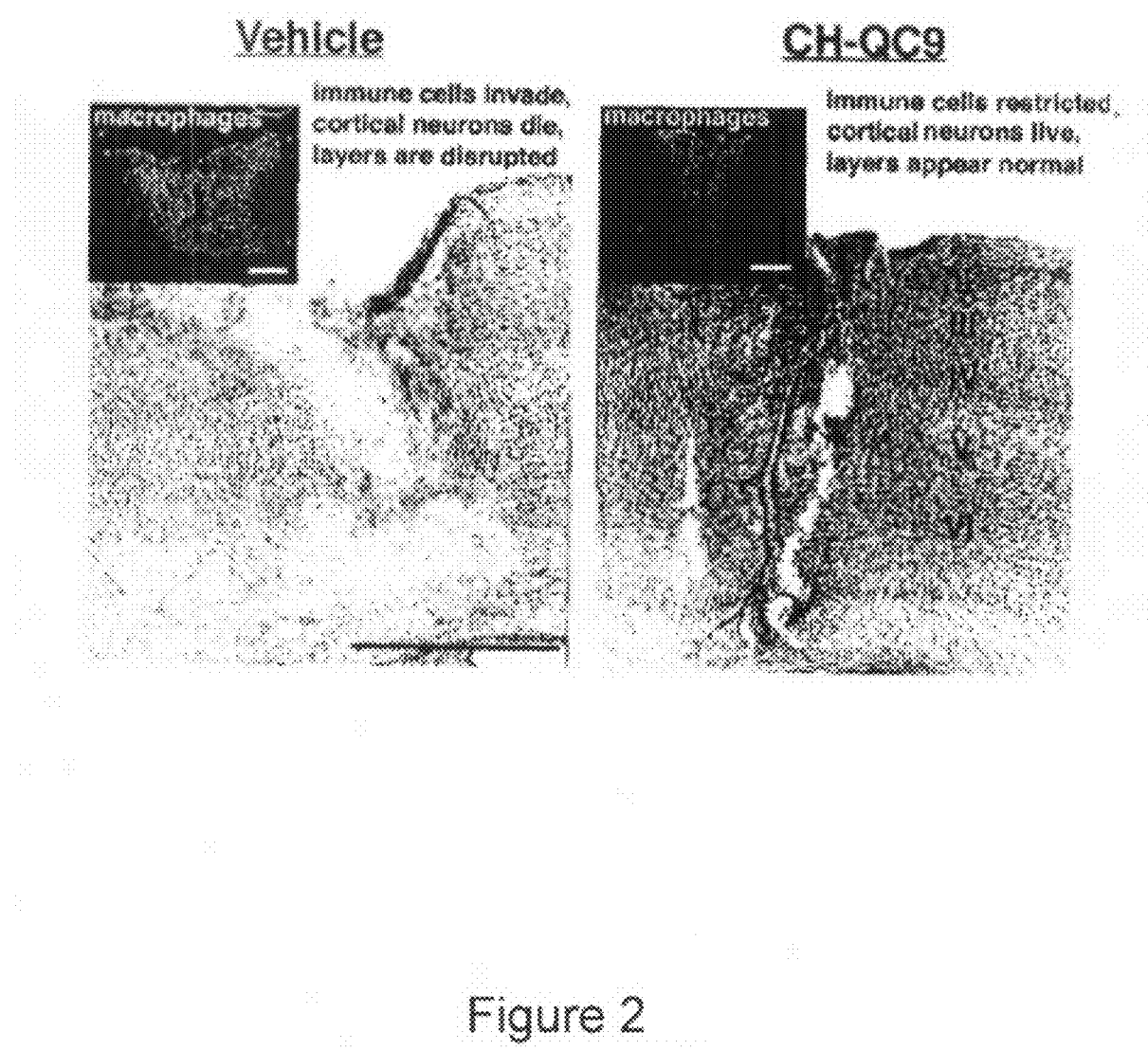
FIG. 2 shows the coronal section through the cerebral cortex of rats that received stab wounds in area 3. The rats survived for 4 days following the lesion after which their brains were processed for cressyl violet staining or immunostaining with macrophage/microglia marker ED-1 in adjacent sections (inset). The vehicle treated animal shows a typical response to the lesion including a pronounced invasion of inflammatory cells and degeneration of cortical tissue. Systemic treatment with CHEC-9 inhibits both processes. Bar=1 mm.

Stab wounds were administered to the rostral cortical area 3 of the exposed cerebral cortex (with dura intact) of rats, using a dissecting knife (blade=1×2 mm). The wound typically produces a significant local inflammatory response, disruption of the functional layers of the cortex, and marked atrophy and degeneration of neurons (FIG. 2, left panel). The principal immune cells involved in the inflammatory response are macrophages and microglia (FIG. 2, inset). Subcutaneous injection of CHEC-9 (0.4 mg/Kg bilaterally in the skin of the shoulder), 20 min after the placing of the wound, results in a significant anatomical sparing of the perilesion parenchyma, as well as a more restricted inflammatory response (FIG. 2, right panel).

Activation of Microglia Cells is Inhibited by CHEC-9

Figure 3:
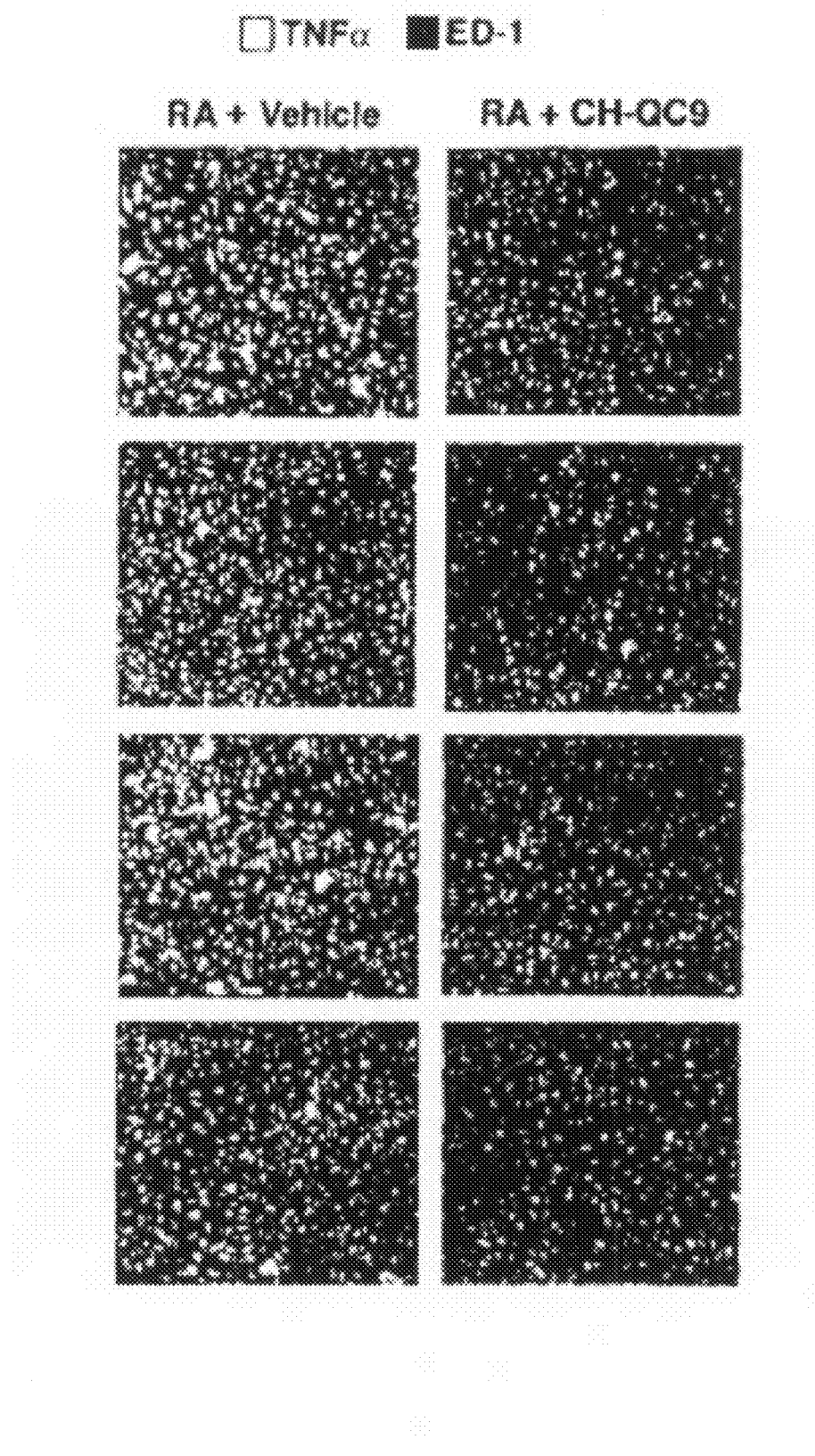
FIG. 3 shows microglia cells which were purified from neonatal rats, activated with 100 nM retinoic acid (RA) on days 1 and 2 in vitro, and examined on day 3 or 4. It is shown that TNFα immunoactivity is reduced in these cells that were treated with 1 nM CHEC-9 during the period of RA activation.
Figure 4:
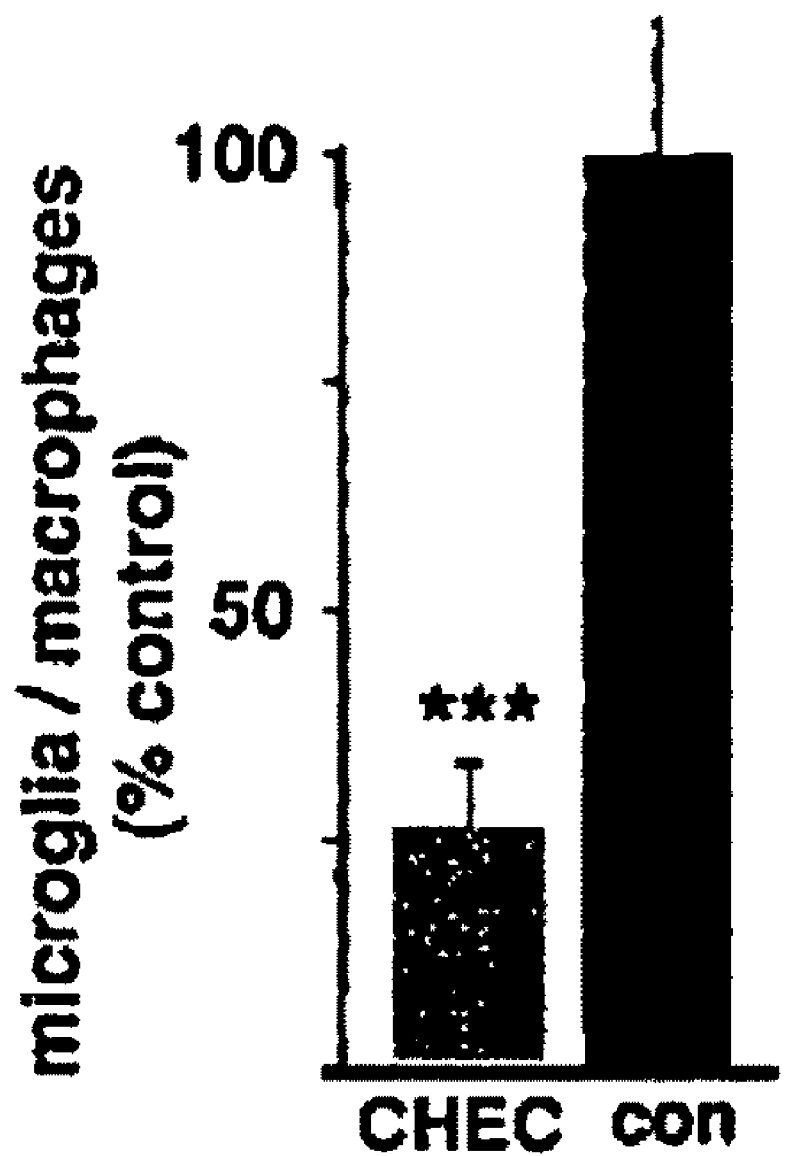
FIG. 4 is a graph showing that percent concentrations of microglia/macrophages at the dorsal and ventral margins of the lesions 4 days after stab wounds to the parietal cortex of rats, are lower in animals which were administered the CHEC-9 peptide. Near marginal or white matter layers, where ameboid cells appeared most consistently in both groups, the number was reduced by 75% (N=6 in each group, $p=4\times10^{-3}$). Such cells are very sparse in the midportions of the lesions after peptide treatment.

Microglia cells were purified from neonatal rats according to established procedures and allowed to develop for an additional 72-96 hrs in vitro, after which the cells are found to be 90-98% ED-1$^+$. ED-1 is a marker specific for rat microglia. Contaminating cells are GFAF+ (suggesting they are astrocytes) or unreactive. TNFα immunoreactivity is at moderate to low levels in these cultures. If, however, the cells are activated with 100 nM retinoic acid on days 1 and 2 in vitro and examined on day 3 or 4, the ED-1 positive microglia cells display rounded morphology with small or blunt processes suggesting that the cells are transformed into amoeboid microglia. (sometimes referred to as brain macrophages, Milligan, et al 1991a; b). TNFα immunoreactivity is more intense in these cultures. These same morphological changes have been described in several studies of microglial activation in vitro (e.g., Siao and Tsirka, 2002, J. Neurosci. 22:3353-3358; Bothatschek, 2001, J. Neurosci. Res. 64:508-522). When the microglia are treated with 1 nM CHEC-9 during the period of activation by RA (30 min after the RA treatment), the cells in the CHEC-9 treated cultures are on average smaller with distinct processes suggesting the transformation to the activated amoeboid morphology is inhibited (data not shown). Likewise, TNFα immunostaining in the cells is reduced. An experiment with eight RA treated cultures is shown in FIG. 3. The 4 cultures in the right panels were also treated with 1 nM CHEC-9 peptide.

CHEC-9 Protects Neural Cells and Inhibits Inflammation

All animal procedures were in compliance with the relevant laws and institutional guidelines, and were approved by Animal Care and Use Committee of Drexel University College of Medicine. The lesion studies were conducted on 15 long evans hooded rats weighing 225-275 g. Twelve of these rats were deeply anesthetized with ketamine/xylazine and placed in a stereotaxic holder. A 4×2 mm (rostrocaudal× mediolateral) skull opening was made on the right side starting just behind the coronal suture and centered at a mediolateral position of +2.5 mm relative to bregma. A dissecting knife was penetrated through the dura and cortex in the center of this skull opening to a depth of 1 mm. The skull defect was filled with bone wax, the skin sutured closed, and the animal placed on a heating pad. Twenty minutes later, 0.4 cc of solution containing 100 μg of peptide (~0.4 mg/kg, 6 rats) or DMEM vehicle (6 rats) was injected under the skin of the shoulder near the midline. The rats were perfused 4 days later and their brains processed for histology and immunohistochemistry as in previous studies. Three rats were sacrificed without surgery or treatment. Alternate coronal sections of these brains were stained with cresyl violet acetate and immunostained with the TUJ1 antibody to neuronal specific tublin, isotype III (Covance Research Products) or monocyte marker ED-1 Serotec. Secondary antibodies were FITC or Rhodamine conjugated (Jackson Immunolabs). The density of ED-1+ ameboid microglia in the perilesion parencyma wound was calculated after experimentally blinded counting of 4 fields (dorsal and ventral margins of the wound) in 2 sections through the lesion.

Four days following perfusion, there were no obvious behavioral differences between the treated and untreated groups. Both displayed normal locomotor activity and were alert and responsive to orienting stimuli. Cresyl violet-stained sections through the brains of control rats revealed pronounced neuronal degeneration and accumulation of large numbers inflammatory cells in the wound and in the parenchyma surrounding the wound. Immunostaining with the cell specific marker ED-1 showed that many of these cells were macrophages and microglia. The microglia were activated and thus predominantly of the round ameboid type. The cortical layers that are usually obvious in somatosensory area 2 (where the laminae are distinctive) were no longer apparent because of the invasion of these normeuronal cells, and because of the frank degeneration of the neurons. In rats injected with CHEC-9 both the disruption of the cerebral cortex and accumulation of inflammatory cells in the parenchyma was inhibited. This effect was striking and apparent in all the rats treated with the peptide. The most obvious difference found after CHEC-9 treatment was the sparing of the cortical tissue adjacent to the wound in area 2. Granular and pyramidal neurons appeared of near normal size and distribution, and as a result, the cortical layers also appeared normal. In addition, rounded ED-1 positive cells were significantly reduced in the cortex. There were ED-1 reactive profiles scattered in the tissue near the lesion after CHEC-9 treatment, but the vast majority of these appeared to be processes of small, ramified cells, which is the morphology of non-activated or "resting" microglia.

Example 2

CHEC-9 is a Potent Phospholipase A2 Inhibitor, and Inhibits Platelet Aggregation Measurement of PLA2, Platelet Activity.

Trunk blood was collected from 16 additional Long Evans and Sprague Dawley rats of both sexes following decapitation. Fourteen of these rats were paired according to strain, sex, and weight and injected with a control peptide/vehicle or with CHEC-9 forty-five minutes prior to sacrifice. Phospholipase A2 activity was determined in 10 rats and platelets were isolated from the remaining 6 animals.

Serum samples and purified bee venom phospholipase were tested for PLA2 activity using a 1,2-bis(heptanoylthio) glycerophosphocholine substrate (Caymen Chemical) which produces a DTNB reactive sulfhydryl upon cleavage of phospholipids at the at the sn-2 position (target of all PLA2 enzymes). DTNB reactivity with serum, peptides, or PLA2 at the concentrations used in these experiments was not detectable in the absence of substrate (or vice versa). This substrate is sometimes preferred for inhibitor studies since with more natural substrates there is the possibility for interfacial disruptions rather than true inhibition (Mihelich E D, et al., 1997, Prog. Surgery 24:140-145). All reactions were conducted in triplicate or quadruplicate in microwells at 25° with substrate concentrations of 50-500 µM. The measurements were made on an ELX 808 reader (Biotek Instruments) programmable for kinetic studies, and further analysis was performed using nonlinear regression software from Graphpad which fit the data to a hyperbola (one site binding) for determining Vmax and Kd. For experiments with bee venom, CHEC-9, control peptides or tris solvent was mixed with equimolar sPLA2 and incubated at 37° for 30 min. Platelets were isolated from whole blood treated with 1.5 mM EDTA after gradient centrifugation in a 22:5 mixture of Tris glycine buffer and 60% iodixanol (OptiPrep, Axis Sheild). The platelets were washed twice in Hanks balanced salt solution. Peptide was added in the second wash if the animal was untreated, and after an additional 20 min, the medium was collected and dialyzed overnight. Rates of aggregation of the platelets were then determined in response to indicated concentrations of PMA in HBSS by the method of Bednar, et all (1995) in which the absolute value of the rate of change of $A_{650}$ is proportional to rate of aggregation. The dialyzed supernatants were dried resuspended in SDS sample buffer and electrophoresed under reducing and non reducing conditions. Western blots were prepared as in previous studies using a polyclonal antibody to sPLA2 IIa (Caymen Chemical) that is reactive with rats platelet PLA2. Nonparametric statistical analysis (Mann Whitney) was used throughout the study.

Figure 5:
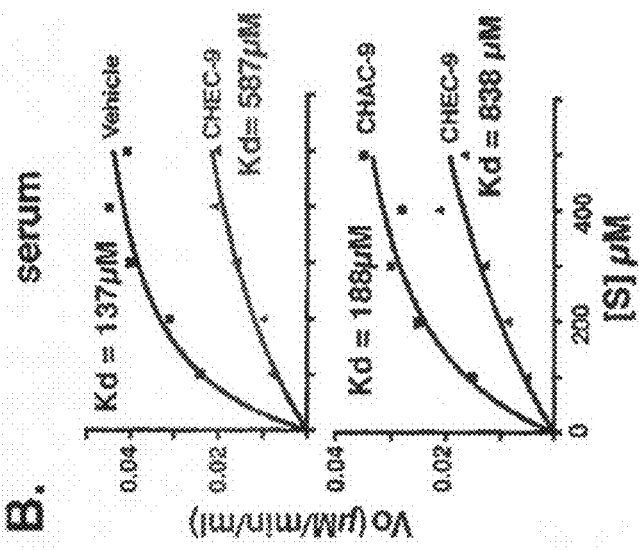
FIGS. 5A-D show that CHEC-9 treatment inhibits PLA2 enzyme and related activities. (A). CHEC-9 inhibition of phospholipase A2 from bee venom is maximal within the first 2 min of the reaction at a variety of peptide concentrations. (B). Representative Michaelis-Menton Plots plot using 5% serum samples from CHEC-9 and control-injected rats. The bottom plot is from a pair of rats in which one was injected with CHEC-9 and one with a peptide where the positions of glutamate and adjacent alanine were switched (CHEC-9). The dissociation constants are noted on the plots. (C). CHEC-9 treatment inhibits platelet aggregation. Platelets were isolated from untreated rats and incubated with 0.1 M CHEC-9 or equivalent tris solvent in HBSS (left graph), or from rats treated with 100 pg CHEC-9 or vehicle (right graph). Rates of aggregation were determined over a period 5-30 minutes after addition of the indicated concentrations of PMA ($p<0.01$, *$p<0.001$. n=10 each in 2 direct treatment and 2 injection experiments). Micrographs of CHEC-9 and control treated platelets at the end of one of the experiments are shown. Bar=100 pm. (D). CHEC-9 treatment results in atypical migration of platelet sPLA2 IIa on SDS gels. Isolation and washing of platelets prior to above analysis caused release of sPLA2 IIa which migrates, as expected, with an apparent molecular weight of ~14 kD on SDS gels run under reducing conditions (lanes 1, 3 control, treated). SPLA2 released from platelets treated with CHEC-9 either 100 pg injected into the animal, (lane 2), or added directly (0.1 n.M) to platelets isolated from untreated rats (lane 4) shows strong sPLA2 IIa bands that run with higher apparent molecular weights. This suggests that treatment had modified the sPLA2 IIa enzyme structure and/or promoted the formation of stabilized enzyme complexes or aggregates.
Figure 5:
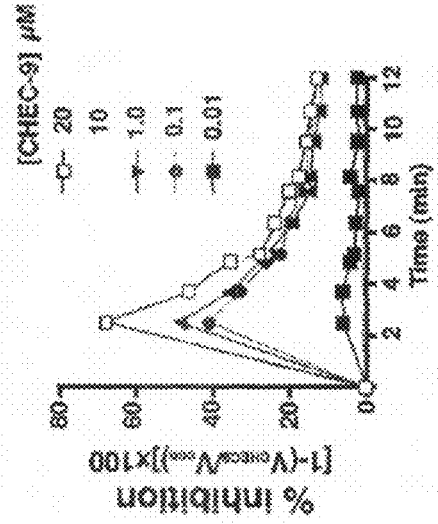
Figure 5:
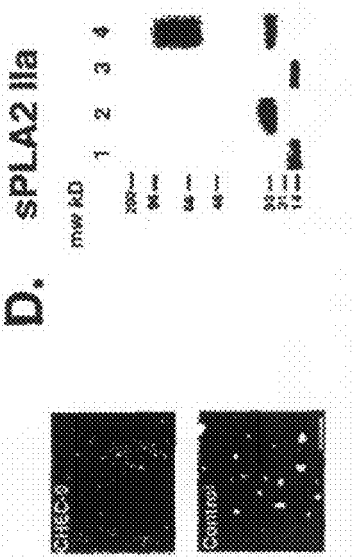
Figure 5:
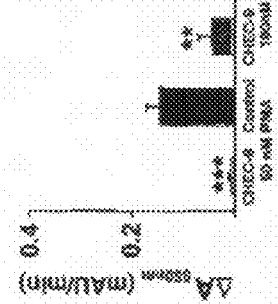

Once its survival-promoting properties were recognized, CHEC-9 was screened in several enzymatic and non-enzymatic assays related to cell survival and immunomodulation. In one of these, the peptide was found to inhibit activity of a secreted phospholipase A2 (sPLA2) derived from bee venom. In these experiments, 70 nM of bee venom sPLA2 was reacted with 50 µM of a glycerophosphocholine substrate in the presence of various concentrations of CHEC-9 (FIG. 5A). The velocity of the reaction was measured and found to be reduced significantly by CHEC-9 at concentrations of 100 nM and above. Next, the PLA2 enzyme activity of serum from peptide and control-injected rats was compared in this same assay after treating the rats according to the regimen used in the lesion studies. Rat serum shows significant phopholipase A2 activity that appears to follow Michaelis-Menten kinetics, at least in the range of serum and substrate concentrations used in these experiments. There was inhibition of the serum PLA2 activity in rats injected with CHEC-9. FIG. 5B shows representative Michaelis-Menten plots using peptide-treated and control sera, including serum of rats treated with a scrambled version of the CHEC-9 peptide. In the latter experiments, it was found that simply inverting the order of the glutamate and the alanine (that is E3-A4 to A3-E4) was sufficient to eliminate the inhibitory activity of CHEC-9. Analysis of kinetic plots from CHEC-9-treated and control rats showed that the peptide, on average, reduced the maximum velocity of the reaction, however this effect was variable and not statistically significant (Vmax CHEC-9=70.3+7.4%, of controls, p=0.132 n=6). The Kd of the reaction was increased in all peptide treated rats, as much as 6-fold, and the difference between peptide and control treated rats was very significant (Kd CHEC-9=313%+68% of controls, p=0.0087, n=6). These experiments provide evidence that the basis for the peptide's inhibition of PLA2 activity in serum is a reduction in the affinity of the enzyme(s) for substrate after treatment.

Platelet activation is a PLA2-related activity and is also affected by CHEC-9 treatment. When platelets are isolated from the blood and then washed, they become activated and begin to aggregate spontaneously. It was observed that this spontaneous aggregation was inhibited by prior treatment with CHEC-9, either using platelets from peptide-injected rats or after direct treatment of isolated platelets with O.lnM CHEC-9 (data not shown). If the platelets are then treated with phorbol-12-myristate-13-acetate (PMA) and agitated, platelet aggregation proceeds at a brisk rate for at least the next 5-30 min, and can be monitored spectrophotometrically. This response is also inhibited for platelets treated with CHEC-9 directly or by injections into rats prior to isolation (FIG. 5C). PMA is suggested to induce platelet activation in concert with mobilization of intracellular calcium by stimulating phosphorylation of cytosolic PLA2 (McNicol A, et al., 1998). It is therefore possible that the peptide effects cytoplasmic PLA2 directly, or indirectly through inhibition of secreted PLA2 enzymes which are released from activated platelets (Han W K, et al., 2003, J. Biol. Chem. 278:24153-24163; Balboa M A, et al., 2003, J. Immunol. 989-994).

While there are likely to be several PLA2 isoforms present in serum, rat platelet sPLA2 (sPLA2 IIa) appears to be abundant in rat serum (Mihelich E D, et al., 1997, Prog. Surg. 24:140-145; Hayakawa M I et al., 1987, J. Biochem. 101: 1311-1314). The release of sPLA2 (IIa) from washed platelets was confirmed by Western blots of platelet supernatants. Interestingly, the sPLA (IIa) released by platelets treated with CHEC-9 (either in the rat or in vitro) produced atypical bands on Western blots, migrating in SDS gels (under reducing conditions) with apparent molecular weights greater than the expected 14 kD (FIG. 5D). The most prominent sPLA2 immunoreactive bands after CHEC-9 treatment migrated above 40 kD, while control rats always showed a 14 kD band, and rarely showed higher molecular weight species. The final position of the sPLA2 bands after CHEC-9 treatment was variable from sample to sample. However, the expected 14 kD species was not observed in CHEC-9 peptide-treated samples, suggesting that treatment had modified the enzyme structure and/or promoted the formation of stabilized enzyme complexes or aggregates. Such aggregates might have a lower affinity for substrate which would explain the kinetic differences in PLA2 reactions found in peptide-treated rats.

Fatty acids, phospholipids, and other lipid mediators of inflammation are increased following brain damage and in neurodegenerative diseases, and much of this increase results from phospholipase A2 activity (Lipton P., 1999, Physiol. Rev. 79:1431-1568; Bazan N G, et al., 2002, Prostaglandins & Other Lipid Mediators in Alzheimer's Disease 68-69:197-201; Lukiw W J, et al., 2000, Neurochem. Res. 25:1173-1184). These products of lipid metabolism, along with the coordinated activity of cytokines and other mediators, contribute significantly to inflammation, and therefore also contribute significantly to neuron death, either that which is observed after acute lesions to the CNS, or that found in many progressive neurodegenerative diseases. In addition, there are numerous examples of cross talk between lipid- and cytokine-mediated inflammatory responses that may amplify these responses especially in the early stages of inflammation (Thommesen L, et al., 1998, J. Immunol. 161:3421-3430; Beck S, et al., 2003, J. Biol. Chem. 278:29799-29812). Finally, the breakdown of phospholipids by PLA2 enzymes produces major changes in membrane function and signaling properties, and leads to increases in free fatty acid production and therefore free radical formation. All these changes are also potentially damaging to neurons and most other cell types.

These experiments indicate that CHEC-9 is effective to treat both acute and chronic neurodegenerative and inflammatory conditions. The peptide's effects on other participants in PLA2-arachidonic acid pathway may prove interesting because many of these are the targets of potential drug therapies for inflammatory disorders in and outside the nervous system. On the other hand, one advantage of upstream inhibition of PLA2, presumably also an advantage for corticosteroids, is that upstream inhibition eliminates the contribution of downstream functionally redundant products or other participants in PLA2-directed metabolism, which may overcome the effects of drugs targeted downstream to more specific elements in these pathways.

Example 3

Anti-Y-P30 Antibody Produces Increase in Cortical Lesion Size and Sera Toxicity

Figure 6:
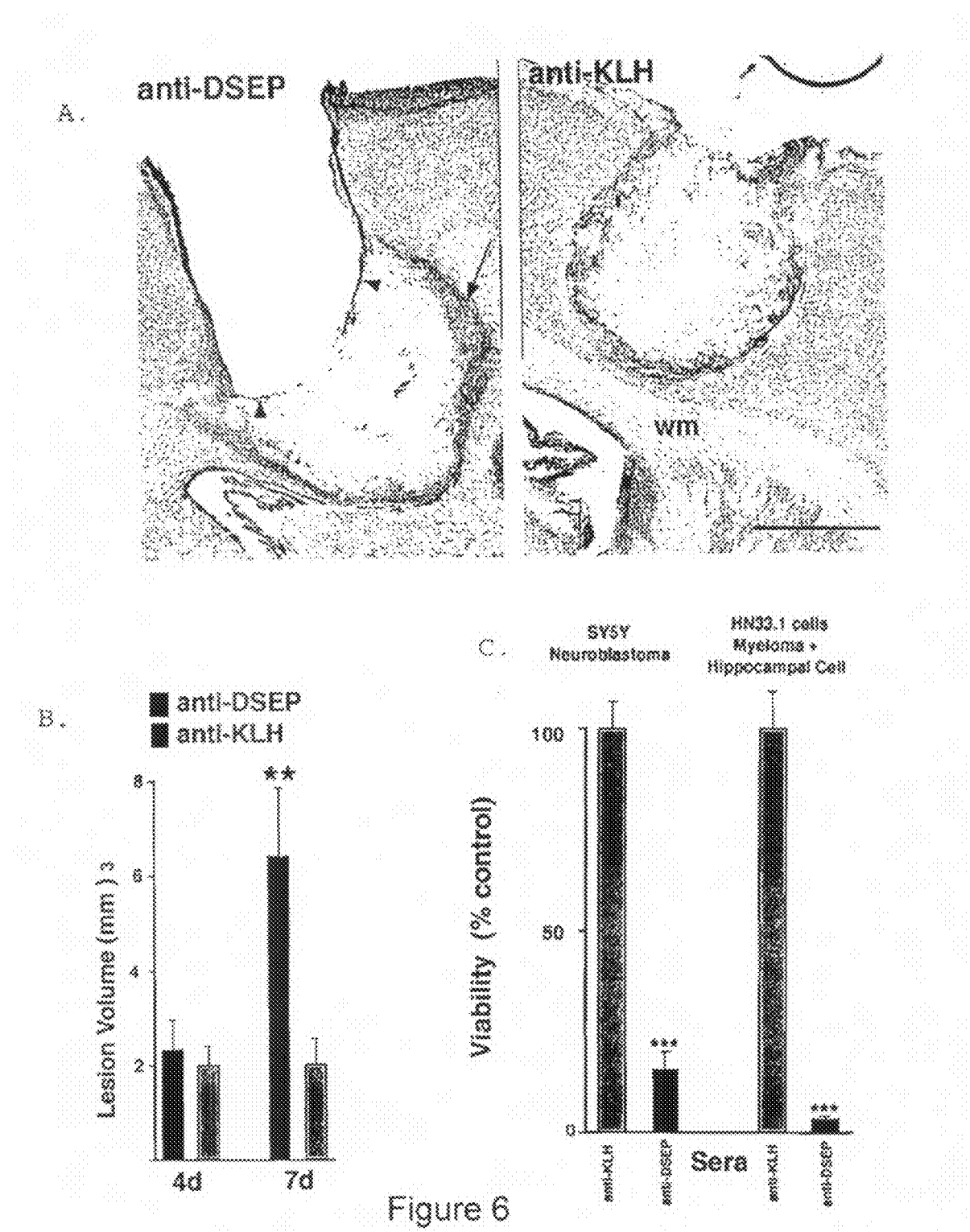
FIGS. 6A-C show that anti-YP30 antibody produces increased cortical lesion size and sera toxicity. (A) Coronal sections through medial part of cerebral cortex seven days after a lesion in area 2 of rats immunized against DSEP-KLH or KLH carrier protein. The lesions are made by placing a 1 mm piece of gelfoam on the cortical surface. There are accumulations of cells at the margins of the lesions (large arrow and arrowheads) many of which are microglia/macrophages. At the 7 day survival, the lesions are considerably larger in rats immunized against DSEP, as can be seen in the photomicrographs and graph of volume measurements from serial sections ($p<0.001$ at 7 days, n=9; n.s.d at 4 days, n=6; A, B). Note also that the lesion in the anti-DSEP rat appears to have expanded from the original boundaries (arrowheads) into the adjacent parenchyma and white matter leaving behind a large cyst. Bar=1 mm. (C) Graph showing killing of SY5Y and HN33.1 cells by DSEP antisera. The cells were treated with 5% serum from rats immunized against DSEP-KLH conjugate or KLH alone (protein concentrations were equivalent). Viability was measured with the WST electrocoupling reagent 72 hrs after treatment and expressed as a percentage of the control value (anti-10 KLH). Cells treated with DSEP antisera degenerate while those treated with anti-KLH do not.

This example demonstrates that there is a DSEPlike polypeptide in the rat brain that cross-reacts with affinity-purified polyclonal anti-human DSEP antibodies (FIG. 6). Rats were immunized with the N terminal peptide of human DSEP (Y-P30) conjugated to Keyhole Limpet Hemocyanin (KLH). Reactivity of their sera to DSEP was confirmed by Western blots and ELISA. Small cortical lesions were produced in the immunized rats. When the rats were sacrificed the extent of damage from the lesion, and the response of macrophages/microglia was tested. Additionally, rat antiserum was tested in a cell viability assay. It was found that DSEP immunized rats have exaggerated cortical lesions and increased cytotoxicity of their sera.

Immunizations, Surgery, Adverse Reactions.

Injections and boosts were subcutaneous, bilaterally in the shoulder over a period of 1.5 months. Control rats were immunized against KLH only. Serum titers of DSEP specific antibodies were measured by ELISA. At the time of sacrifice, titers of the rats used in this study were at least 1:1000 measured in multiple samples (data not shown). In addition, when DSEP antisera were tested in a cell killing assay they were found to be consistently more effective than KLH antisera (see below). Data was collected from 36 rats, 30 of which had small lesions of cortical area 2 near the area 2/3 border. The lesion is produced by stereotaxic positioning of a guide, opening the dura, and placing a 1 $mm^3$ piece of gelfoam on the cortical surface withnlight pressure. Fifteen of these rats were immunized against DSEP-KLH and 15 against KLH alone. Nine rats from each group were sacrificed 7 days after surgery and 6 were sacrificed after 4 days. Four immunized rats (2 from each group) were sacrificed without surgery and two rats were normal. There were no apparent adverse reactions to the immunizations in either group. Gross behavior of all rats was similar. There was no evidence of increased inflammatory reactions peripherally or, after sacrifice, in the CNS of immunized rats without surgery.

Lesion Volumes and ED1 Immunoreactivity

Four and 7 days following surgery, lesion volumes in anti-KLH rats were in a range that was consistent with parallel studies. The differences in lesion sizes were not statistically significant in rats surviving for 4 days (FIG. 6B). However at 7 days following surgery, lesion volumes in rats immunized against DSEP were more than 3-fold larger (FIG. 6A, 6B). The macrophage/microglial response to these lesions was examined after 7 days. As might be expected because of the larger lesions, the anti-DSEP rats had an exaggerated appearance of ED1+ cells at the margins of the lesion and in surviving deep white matter tracts surrounding the lesion (not shown).

Cell Viability Assay.

The antisera from rats immunized with DSEP-KLH were cytotoxic to both HN33.1 and SY5Y cells. Anti-sera from 10 out of the 15 rats in each group was tested at a 1:20 dilution. In all cases, the anti-DSEP sera were clearly more toxic to the cells than the control sera (FIG. 6C). During the first 24 hrs following treatment, sera from both groups caused an apparent injury response and scattered degenerated cells, possibly due to complement-mediated mechanisms. Heating the sera for 30 or 60 min at 55" to destroy complement had variable effects on the cultures but tended to improve this initial response. By 48-72 hrs the cells treated with anti-KLH sera had mostly recovered while the cells treated with the anti-DSEP were degenerated completely.

Example 4

CHEC-7 and CHEC-9 Inhibit sPLA2 Response to Lipopolysaccharide from *E. Coli*

Figure 7:
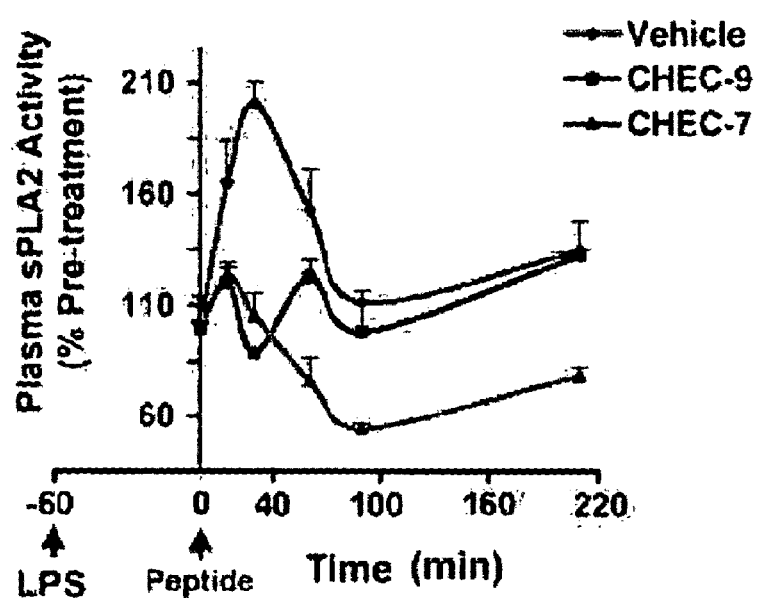
FIG. 7 is a chart depicting the effect of CHEC-7 and CHEC-9 on sPLA2 activity. CHEC-7 and CHEC-9 were administered subcutaneously 60 minutes after subcutaneous administration of LPS. Plasma levels of sPLA2 were measured at the time points indicated.

Adult female Sprauge-Dawly rats were injected with 4 mg/kg of lipopolysaccharide (LPS) subcutaneously. Sixty minutes later, either CHEC-7 or CHEC-9 peptide (at 0.4 mg/kg) were also injected also subcutaneously. Plasma sPLA2 activity was measured at the times indicated in FIG. 7. CHEC-7 (CHEASQC, SEQ ID NO.: 3), has adjacent alanines removed as compared to CHEC-9 (SEQ ID NO.: 1). Both peptides were cyclized prior to use. Both are effective in attenuating LPS-induced increases in sPLA2 activity in plasma, though CHEC-7 had a greater and more sustained effect.

Example 5

CHEC-7 and CHEC-9 Inhibit PLA2 Activity in Human Plasma

Figure 8:
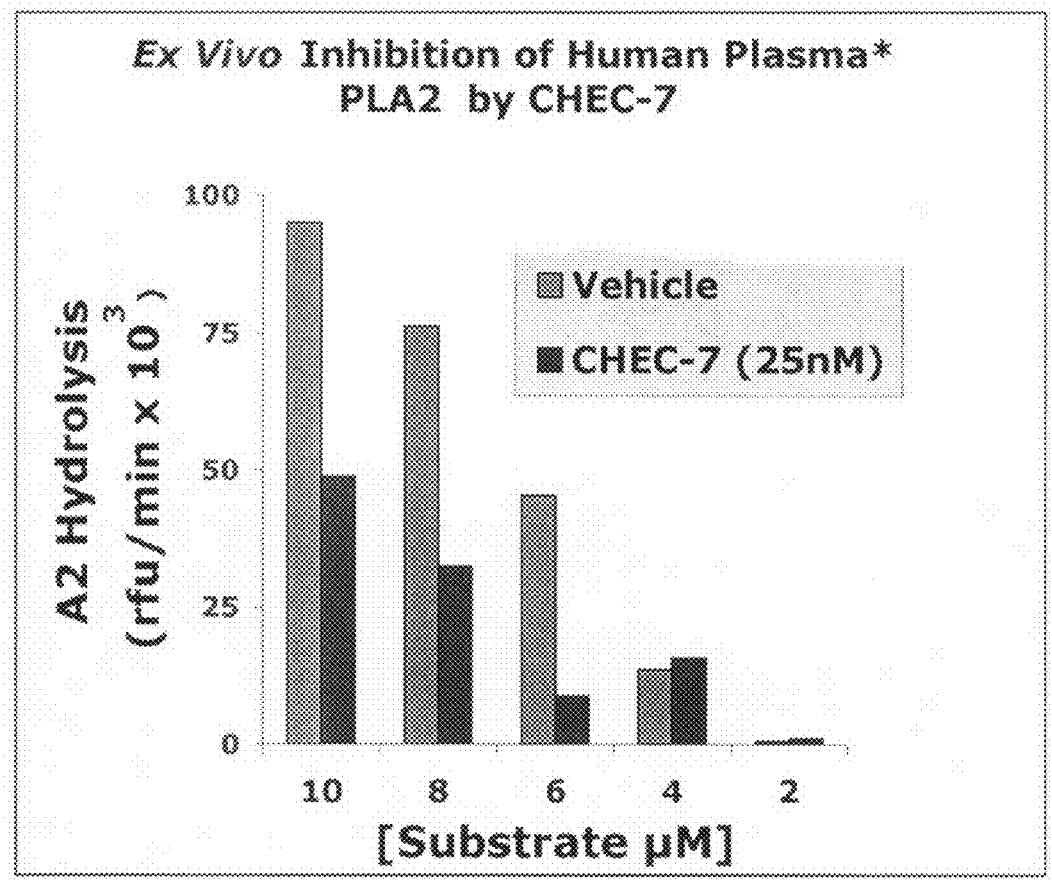
FIG. 8 is a chart depicting ex vivo inhibition of human plasma PLA2 by CHEC-7. The reaction mixture also contained 25 nM CHEC-7 (or vehicle) and the PLA2 substrate N-((6-(2,4-dinitrophenyl)amino)hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6, Invitrogen).
Figure 9:
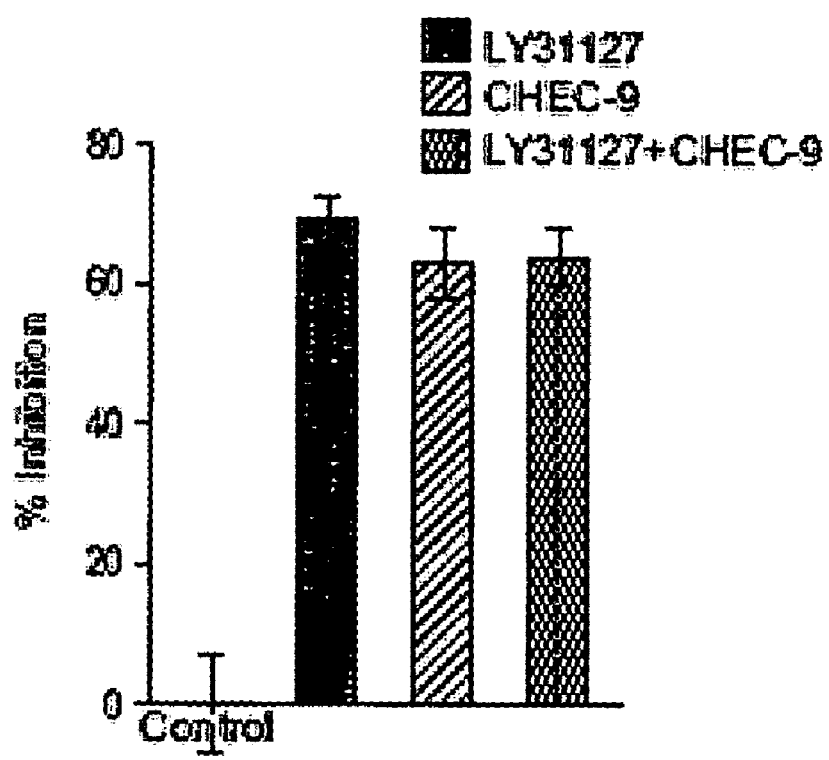
FIG. 9 illustrates how whole human blood was collected from a healthy 42 yr. old female volunteer and incubated at 40 for two 90 min periods with vehicle (control), CHEC-9 (0.4 µM) followed by vehicle (CHEC-9), LY31127 (5.0 µM) followed by vehicle (LY31127), or CHEC-9 followed by LY31127 (LY31127+CHEC-9). Inhibition was calculated by comparison with control velocity [$(1-V_{inh}/V_{con})\times100$]. Data shows the mean values for 4 enzyme reactions per condition. CHEC-9 and LY31127 at these concentrations appear to be equally effective inhibitors that are non-additive under these experimental conditions.

Plasma (25% final concentration) is pooled from 10 ALS patients. Patient plasma was used because of high baseline activity, compared to age-matched control plasma, which is preferred condition for peptide inhibition (Cunningham, et al., J. Neuroinflammation. 2006, 3(1):25)). The reaction mixture also contained 25 nM CHEC-7 (or vehicle) and the PLA2 substrate N-((6-(2,4-dinitrophenyl)amino)hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6, Invitrogen). Hydrolysis of the A2 bond, targeted by PLA2 enzymes, unmasks an internally quenched fluorescent signal (rfu) that serves as a measure of enzyme activity. This substrate reacts with both sPLA2s and cPLA2 enzymes although the latter is expected to be sparse in plasma (FIG. 8). It appears that the CHEC-7 peptide is less effective at the lowest substrate concentrations so like CHEC-9 may have properties of an uncompetitive inhibitor (ibid).
CHEC-9 inhibits sPLA2 activity in human plasma samples after treatment of whole blood ex vivo. These experiments were conducted to determine whether CHEC-9 inhibits sPLA2 activity in human blood. Whole blood from 4 healthy volunteers (2M, 2F 36-57 yo) was collected by venipucture in Citrate Phosphate Dextrose (CPD) anticoagulant and divided for treatment of equal volumes with either CHEC-9 or vehicle (50 mM Tris, pH=7.4). Treatment was at 4° with gentle rocking for 2 hrs. Plasma samples were prepared by centrifugation and reacted with a glycerophosphocholine substrate specific for sPLA2 (Caymen Chemical). All samples treated with CHEC-9 showed inhibition of sPLA2 activity (50-80%). Final peptide concentration in plasma was 200-400 nM.
CHEC-9 inhibition of sPLA2 activity in human plasma samples is comparable to that of Lilly designer sPLA2 IIa inhibitor LY31127. CHEC-9 was compared side by side with LY31227. This small molecule inhibitor was designed on the basis of sPLA2 IIa active site structure and is presently under consideration for non nervous system anti-inflammatory therapy. Both inhibitors were applied to whole human blood where the group II isoforms are predominant (FIG. 9). CHEC-9 and LY31227 gave similar results. The effect of the inhibitors was calculated by assuming the inhibition in the control samples was zero (see legend for FIG. 9). The effects of LY31227 and CHEC-9 were non-additive, suggesting either that they target a similar pool of enzyme in serum or there are complex interactions between the two inhibitors and/or their targets.

Example 6

Systemic CHEC-9 Inhibits sPLA2 Enzyme Activity in Whole Cortical Cell Membranes of Saline-Perfused Normal Rats These studies were undertaken to determine whether systemic CHEC-9 would effect sPLA2 activity in CNS tissue of unoperated rats, thus suggesting that the peptide's influence was not blocked by the blood brain barrier. The results suggested that when whole membranes of saline perfused rats were tested, CHEC-9 injections produced significant inhibition of sPLA2 activity under the conditions used herein. Tissue preparations from cerebral cortex homogenates of normal rats that had been injected with 0.4 mg/kg CHEC-9 were tested, at the dosage of the peptide used in the lesion studies. These extracts were prepared as in previous studies (Cunningham, et al., 2000, Exp. Neurol. 163:457-468) and included cytosol, CHAPS solubilized membranes, with and without a prior salt wash, and whole membranes, i.e. non-solubilized, after salt wash. In addition, protease inhibitors were added or omitted at different stages of these preparations. The most consistent sPLA2 activity and CHEC-9 inhibition was found in salt washed whole membranes without protease inhibitors in these final samples, compared to for example, CHAPS solubilized membranes with protease inhibitors. This procedure has therefore been used in all recent studies. Pete, et al., (1996, Biochim. Biophys. Acta. 1299:325-332) report that the protease inhibitor PMSF also inhibits PLA2 activity.

Example 7

CHEC-9 Treatment of Experimental Autoimmune Encephalitis

A study was conducted using 10 Dark Agouti rats immunized bilaterally in the foot pads with guinea pig myelin basic protein emulsified with complete Freund's adjuvant. As described by others (Milicevic, et al., 2003, J. Neurosci. Res. 72:268-278), this procedure in DA rats induces a moderate but consistent EAE response after 10-15 days which is characterized by tail and limb paresis/paralysis. Experiments lasted 18 days following immunization, during which time the rats were weighed and scored for clinical disease daily. Post-immunization (PI) changes in sPLA2 activity in urine was monitored as a potential guide to an appropriate CHEC-9 treatment regimen (FIG. 10). Treatment with CHEC-9 or vehicle was begun on day 5 PI when there was a significant peak in urinary aPLA2 activity. The rats were then treated for 10 days with 60 μg peptide (first day) and 30 μg (subsequent days) in 200 μl delivered subcutaneously (~0.4 and 0.2 mg/kg respectively). For blinded treatment and observations both the animals and syringes were coded. The sPLA2 response at 4-8 days PI was followed by decline of average activity over the next four days. This drop in activity was significant for CHEC-9 treated rats but not vehicle treated rats (FIG. 10).

Urine samples were also prepared for SDS page and immunoblotting in order to assay for neurofilament. These experiments represent an attempt to provide a non-invasive measure of neuron/axon loss by semi-quantitative Western analysis. So far the analysis has been limited to the usually 160 kD neurofilament M. Although the specific fragments of this protein that appear in urine are variable depending on the model, consistent increases were found in one or more of these fragments under conditions where neuron/axon death might be expected.

Foot edema caused by MBP/CFA injections was measured (FIG. 11). These blinded measurements were made on PI day 10, after 5 days of treatment. Rats treated with the peptide had reduced or no swelling of the feet. Since foot thickness was not measured continuously post immunization, the relative contributions of inhibition and reversal of the edema by CHEC-9 are not clear at present. Nonetheless, these experiments suggest that CHEC-9 has peripheral anti-inflammatory/immunosuppressive properties that may contribute to its effectiveness in the present experiments, and in other applications and indications.

Figure 12:
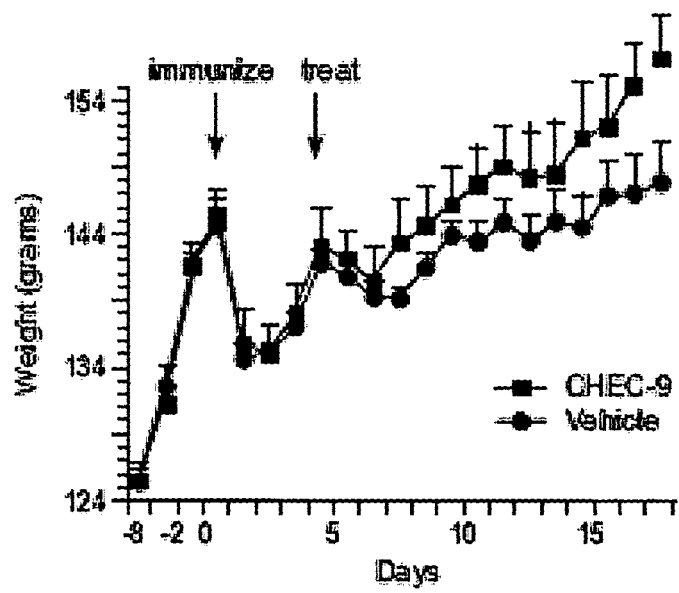
FIG. 12 shows the body weight of DA rats immunized with guinea pig myelin basic protein in CFA. The rats added weight normally prior to immunization after which there was an expected precipitous decline. CHEC-9/vehicle treatment began 5 days after immunization. CHEC-9-treated rats add body weight at a significantly higher rate than the vehicle-treated rats during the period when the latter developed EAE symptoms.
Figure 13:
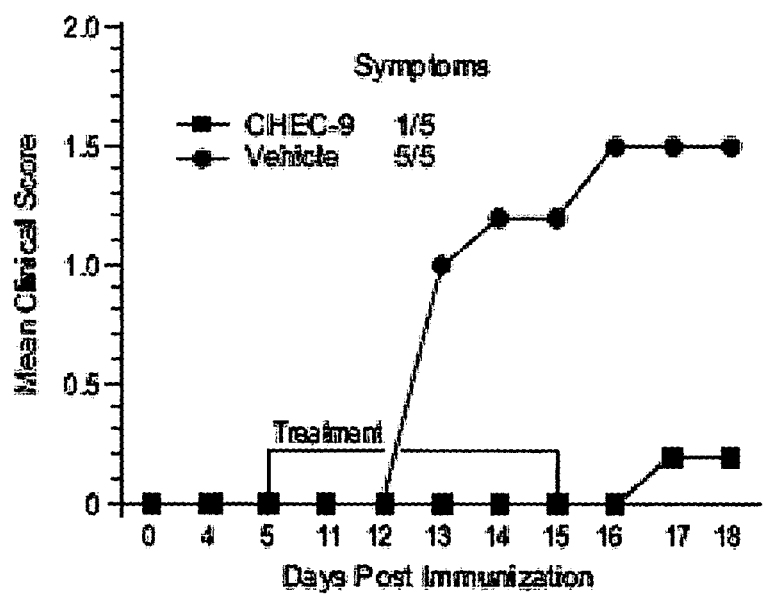
FIG. 13 shows the development of EAE symptoms in DA rats immunized with guinea pig myelin basic protein/CFA. The rats were treated with CHEC-9 or vehicle for 10 days starting on PI day 5. They were scored daily on a 0-4 EAE scale (see Methods) by two separate investigators who did not know the experimental categories. All vehicle treated rats developed symptoms, 3 with hindlimb involvement. One of the CHEC-9 treated rats developed a weak tail on PI day 17.
Figure 15:
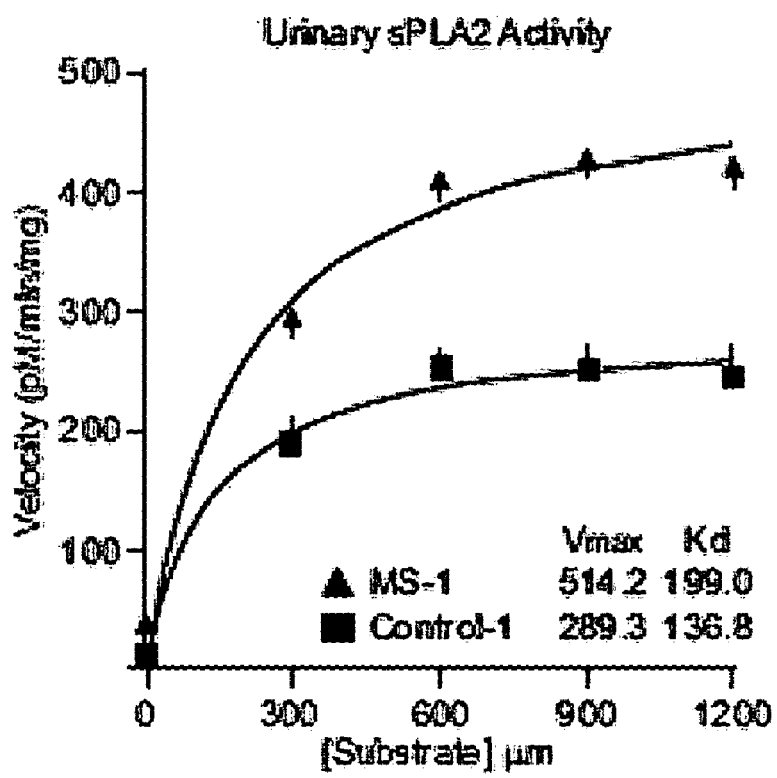
FIG. 15 is a graph depicting urinary sPLA2 activity, wherein urine samples were collected mid morning from a patient with Multiple Sclerosis (MS-1) and an age/gender matched healthy control (Control-1). The urine was sterile filtered and triplicate 25 μl samples were reacted with different concentrations of a thio-glycerophosphocholine substrate in the presence of Ca2+. This substrate is specific for sPLA2 activity. The reactions showed typical Michaelis-Menton enzyme kinetics under these conditions. The patient was in static phase (non relapsing), the last relapse occurring in October of 2004. The patient was not involved in any immunomodulatory therapy and neither patient nor control volunteer had engaged in strenuous physical activity or taken NSAIDs in the last 24 hrs.

FIGS. 12 and 13 show the results of daily weight measures and EAE clinical scoring in the pilot study. These data were collected in an experimentally blinded manner. The results of both measurements showed that CHEC-9 treatment prevented the onset of disease in all but one rat that had late onset tail weakness. The rate of weight gain after CHEC-9 treatment was accelerated in the peptide treated rats.

One spinal cord was sectioned from each group through the region of the conus medullaris and stained for Nissl-myelin. The peptide treated rat (#411) showed no deficits and the vehicle treated rat (#410) scored 2.5 (tail flop, one paralyzed and on paretic limb). There were marked obvious differences in the histology of caudal spinal cord between these two rats—several millimeters of the caudal-most spinal cord was severely atrophic in rat 410. The sections revealed that there was extensive cell shrinkage and/or small cell invasion as well large regions of dense degenerating myelin (FIG. 14). Rat 411 had small areas of degenerating myelin but little apparent atrophy either of the cord or of the cells. These results are consistent with the clinical scores of the two rats.

Example 8

Studies of PLA2 Activity in MS Patients and Potential Role of CHEC-9 in Therapy sPLA2 activity is measured in plasma and urine samples from patients with relapsing/remitting Multiple Sclerosis and compared to samples from healthy controls. The patient population consists of individuals in both active and static disease states and includes MS patients not on treatment studied at baseline, as well as those in defined treatment paradigms. EDSS and MSFC disability scores are measured for comparison with sPLA2 levels. A fraction of each blood sample is incubated with CHEC-9 to determine whether the peptide inhibits sPLA2 activity in MS (as it does after treatment of whole blood of healthy volunteers). Downstream AA metabolites and multiple cytokines are measured in the plasma samples with and without prior CHEC-9 treatment. Forty-four patients with a diagnosis of relapsing/remitting Multiple Sclerosis provided urine samples for the study (Table 2).

TABLE 1

Range of MS patient data.

| Group | n (F/M) | Age yrs ± sd | MS Onset yrs ± sd | MS Duration yrs ± sd | βIF | GA | None |
|---|---|---|---|---|---|---|---|
| Active | 12 (8/4) | 38.2 ± 9.5 | 29.5 ± 8.9 | 7.3 ± 4.5 | 9 | 1 | 2 |
| Stable | 32 (25/7) | 43.6 ± 8.1 | 33.4 ± 8.6 | 10.6 ± 9.3 | 15 | 3 | 14 |
| Control | 14 (9/5) | 37.5 ± 9.0 | — | — | — | — | — |

F/M = female/male;
βIF = beta Interferon;
GA = glatiramer acetate;
sd = standard deviation Healthy controls were recruited by advertisement. The Institutional Review Boards of Drexel University and Graduate Hospital of Philadelphia approved the study and informed consent was obtained from all subjects. Twelve of the patients presented with active disease at the time of sample collection, which was defined as a change of one or more points on the functional neurologic status score in the absence of fever or infection. Therapies noted in Table I were interferon beta-1a (Avonex®, Biogen, 30 µg/week I.M.) or glatiramer acetate (Copaxone®, Teva Pharmaceutical Industries 20 mg/day, S.C.). Subjects with peripheral infections or inflammatory disorders, or those using anti-inflammatory drugs within the 24 hours prior to sample collection, were excluded from the study.

EAE Production and Analysis. The animal experiments were conducted under the auspices of an approved IACUC protocol from Drexel University. All personnel involved were experimentally blinded for all procedures. Mild to moderate EAE was induced in 20 female Dark Agouti rats (130-150 g) by bilateral foot pad immunizations of 100 µg guinea pig myelin basic protein in saline emulsified with Complete Freund's Adjuvant. The rats were weighed and scored for EAE symptoms daily using a 1-4 rating scale for clinical disease (1-tail drop, 2 hind limb paresis, 3 hind limb paralysis, 4 moribund). A score of 2.5 was given for complete paralysis of one hind limb, which was the most severe disease encountered in this experimental system. The experiments lasted 18 days following immunization, after which the rats were perfused with 4% paraformaldehyde in 0.1M phosphate buffer and their spinal cords removed for histology.

Urine collection and CHEC-9 treatment. Urine was collected in metabolic cages from all rats starting 1-2 days before immunization and then every other day for 18 days. CHEC-9 treatment started 5 days after immunization during the rise in urinary PLA2 activity. Treatment consisted of a subcutaneous injection of 60 µg CHEC-9 in clear DMEM vehicle on the first day, followed by daily 30 µg doses for 9 days. CHEC-9, CHEASAAQC, was made by Celtek (Nashville, Tenn.), purified and cross-linked as described previously.

PLA2 enzyme activity. Twenty-five µl samples of (0.2 µm) filtered urine were reacted with 1,2-bis(heptanoylthio) glycerophosphocholine, a substrate for PLA2s with the exception of cPLA2 and PAF-AH (Caymen Chemical, Ann Arbor Mich.). Reaction buffer consisted of 50 mM tris, 0.1M NaCl (pH=7.4) containing 1 mM DTNB (Ellman's reagent) and 2 mM $CaCl_2$. Rates and kinetic parameters were determined by a Deltasoft (Princeton N.J.) supported ELX 808 reader (Biotek, Burlington Vt.) and non-linear regression software from Graphpad (San Diego Calif.), and expressed relative to total protein in the samples. Selected urine samples were dialyzed in 1 kD membranes against 20 mM tris and prepared for Western blotting as in previous studies. SDS PAGE prior to blotting was under reducing conditions. Blots were reacted with a polyclonal antibody directed against human sPLA2 IIa (Caymen Chemical). All data comparisons were by a two-tailed Mann Whitney test or nonparametric (Spearmann) linear correlation.

Other assays were conducted at ambient temperature (22-25°) using a Victor 3 fluorescent reader (Perkin Elmer, Nutley N.J.). The substrate was 1-Palmitoyl-2-Pyrenedecanoyl Phosphatidylcholine ("10-pyrene", Caymen Chemical, Ann Arbor Mich.) a substrate for all calcium dependent PLA2s with the exception of cPLA2 and PAF. The substrate (supplied in chloroform) was dried under a nitrogen stream, quickly dissolved in ethanol, and stored at −20° prior to use. Substrate solutions were prepared in reaction buffer consisting of 50 mM tris (pH=7.4), 0.1M NaCl, 2 mM $CaCl_2$, 0.25% fatty acid-free albumin (Sigma) and the CHEC-9 peptide at the indicated concentrations. CHEC-9 (CHEASAAQC) was synthesized by Celtek, (Nashville, Tenn.), purified and cross-linked as described previously (see Cunningham, et al 2004), and aliquots stored in tris buffer or DMEM vehicles at −80°. The 10-pyrene substrate forms phospholipids vesicles in aqueous solutions, and upon hydrolysis, releases 10-pyrenyl-decanoic acid. This product is fluorescent in the presence of albumin and was measured at 350 nm excitation, 405 nM emission. Plasma samples were 20% final concentration in the reaction mixture, and all enzyme reactions were initiated with the addition of the substrate solution to the sPLA2 containing samples. Kinetic parameters including the properties of CHEC-9 were determined by measuring the initial velocities ($V_o$) of enzyme reactions (within 1 minute of initiation). For experiments in which active sPLA2 enzyme concentration was measured in plasma samples from peptide-treated rats, we used a single substrate concentration and measured the steady-state rate of the enzyme reaction for 30 minutes. This rate is proportional to the concentration of active enzyme in the plasma if product, formation during this period is linear with respect to time. In most experiments, relative fluorescent units (RFU) were converted to product concentration using a pyrenyldecanoic acid standard curve (Molecular Probes, Eugene, Oreg.). For plasma, the background fluorescence of the plasma was not subtracted, but this did not effect the velocity measurements. Individual reactions were carried out in duplicate or triplicate and kinetic curves were produced using 5-6 substrate concentrations, with or without peptide, reacted simultaneously. Representative Lineweaver-Burke plots and nonlinear regression analyses are presented in Results, only after repeating an experiment 5 or more times with the same result, i.e., the direction of change of Km and Vmax was the same following inhibitor treatment, and $K_i$ was less than 100 nM. Km and Vmax were determined with nonlinear regression software (Prism) from Graphpad (San Diego, Calif.).

Results of MS and EAE studies. Filtered urine follows typical Michaelis-Menton reaction kinetics indicating that measurements of velocity at saturating substrate concentrations are proportional to the concentration of active enzyme present in the sample (FIG. 16A). The average sPLA2 activity is significantly elevated in the urine of patients with both active and stable MS (FIG. 16B). The mean activity was higher in relapsing patients compared to non-relapsing patients although the difference did not reach statistical significance (p=0.107). Interestingly, there was no difference in the mean activity of stable patients receiving no treatment and those treated with beta interferon (mean 393±130% of control n=15, versus 409±98% s.e.m., n=14, p=0.585). However these patients are heterogeneous with respect to PLA2 levels as suggested by the high variances in the measurements. Importantly, PLA2 activity does not correlate with total urinary protein in any group, so it is unlikely that the patients simply leak more PLA2 because of some previously unrecognized deficit in renal function (p values for protein-PLA2 correlation, Active=0.572; Stable=0.350; Control=0.885). We also found that dialyzed and concentrated samples (200 μg total protein) were immunoreactive for the 14 kD group IIa PLA2 species, suggesting that whole PLA2 molecules (at least for this isoform) are excreted (FIG. 16A, inset).

There was an initial loss of body weight post-immunization (PI) in both CHEC-9 and vehicle treated rats. From post-immunization day 5 (the start of treatment) onward, peptide treated animals gained weight at a significantly higher rate than vehicle treated rats (0.517 g/day vs. 0.392 g/day, p=0.002 paired test of daily averages). Mean urinary PLA2 activity increased for the first 8 days PI in both groups of rats (FIG. 17A). CHEC-9 treatment resulted in a significant decline in activity between by days 8 and 10, just prior to the onset of the behavioral deficits (FIG. 17B). However, only 3/10 peptide-treated rats showed symptoms of disease and one of these had a late onset tail paresis (at day 17 post-immunization). This compares to 8/10 in the vehicle treated group showing generally more severe symptoms that appeared between days 10 and 13 PI. Nissl/myelin and Hemotoxylin and Eosin staining through the caudal-most spinal cord revealed pathology consistent with the clinical score. Large regions of densely packed small cells appeared in rats showing the most severe deficits (clinical score 2.0 or greater), presumably the result of perivascular effusion of peripheral immune cells).

PLA2 enzyme activity is increased in the urine of subjects with either active or stable MS, suggesting that these patients had increased levels of systemically active enzyme. It was somewhat surprising to find that PLA2 enzymes in urine react with substrate according to a typical hyperbolic function, but this result increases confidence that the measurements reflect levels of active enzyme. Furthermore, the same increase was found in rats following immunizations that produced EAE. Although the validity of EAE as a model for MS has been questioned, it is still useful in the present context to help define the role of PLA2 activity in the progress of autoimmune pathologies involving the nervous system. The attenuation of EAE by PLA2 inhibitor CHEC-9, along with similar results by others, also argues for a significant role for these enzymes in MS and related disorders. Interestingly, the effects of CHEC-9 were detected only at the peak of PLA2 activity, a few days after the start of treatment. Recent experiments suggest that CHEC-9 exhibits several properties of an uncompetitive inhibitor (i.e. it may bind the enzyme-substrate complex) when tested with purified sPLA2 group I and with human or rat plasma ex vivo. Therefore, the peptide may be effective with high enzyme-substrate availability, as would be expected during periods of excessive inflammation or oxidative stress, which could explain the delayed PLA2 response.

The therapeutic effects of CHEC-9 in EAE may be related to a decrease in PLA2-directed inflammation, or to a reduction in PLA2 potentiated excitoxicity. It is also possible that specific immunoregulatory functions of PLA2 enzymes are affected. Secreted PLA2s regulate T lymphocyte activity and levels of proinflammatory cytokines in a variety of cell types (either directly or via cytosolic PLA2), especially during periods of oxidative stress.

The results set forth herein suggest that further study of PLA2 regulated processes in EAE models may provide new insights into therapies for autoimmune disorders affecting the nervous system. Furthermore, monitoring PLA2 activity in MS patients, for example in relation to their susceptibility to relapse, could help define appropriate regimens for application of these new therapies.

The disclosure set forth herein also indicates that increased levels of sPLA2 enzymes, long associated with inflammation outside the nervous system, also characterize Multiple Sclerosis and Experimental Autoimmune Encephalomyelitis. Although the EAE model has been questioned recently in terms of its validity for identifying potential MS therapies, the model is clearly useful to help define the role of inflammatory enzymes, specifically the PLA2s, in autoimmune attack of the nervous system. Using a simple urinary assay for active enzyme concentration, it was demonstrated that rats immunized to produce EAE had increased systemic sPLA2 following immunization. The same assay applied to samples collected from MS patients also showed increased enzyme levels even with random or "spot" sampling. Based in part on the parallel results in the rodent model, it was concluded that sPLA2 inflammatory activity is ongoing in the majority of MS patients, active or stable, regardless of treatment. The highest levels of enzyme were found in patients with active disease, i.e., during relapse. Interestingly, asymptomatic EAE rats had elevated enzyme activity but became symptomatic only after the peak in measured activity, suggesting that elevated enzyme activity and behavioural deficits are correlated. Finally, and most important, EAE symptoms were attenuated by sPLA2 inhibitor CHEC-9. This finding supports the idea that PLA2 enzymes play a direct role in the pathogenesis of MS and related autoimmune disorders.

The kinetics of CHEC-9 inhibition of sPLA2 suggest that the peptide exhibits several properties of an uncompetitive inhibitor, which may help explain the delay between treatment and the ability to detect a reduction in enzyme activity. Since uncompetitive inhibitors depend on sufficient levels enzyme and substrate, it may be that those levels were not appropriate (at least for the present CHEC-9 dosage and treatment schedule) until sPLA2 activity was maximal, several days after the start of peptide treatment. In addition, it is under these conditions of inflammation and oxidative stress that sPLA2 may exert the most profound effects on the activity of cytosolic PLA2 (cPLA2). The specific involvement of cPLA2 in EAE has also been demonstrated. A straightforward explanation of the therapeutic effects of CHEC-9 is that peptide inhibition decreases sPLA2-mediated inflammation and the inflammatory products of PLA2 metabolism, either directly or via cross talk with cPLA2. Studies are in progress to test this proposition with reference to specific downstream products in PLA2 pathways. There are other properties of these enzymes that may be involved in regulating neuron viability and both innate and acquired immune responses. For example, sPLA2 enzymes potentiate excitoxicity, a mechanism suggested to be involved in most instances of neurodegeneration. In addition, there are specific immunoregulatory functions of PLA2 enzymes that may be affected by this inhibitor. Secreted PLA2s regulate T lymphocyte activity and levels of proinflammatory cytokines in a variety of cell types (either directly or via cPLA2), especially during periods of oxidative stress. Thus, sPLA2 enzymes may be an important therapeutic target for a variety neurodegenerative disorders, particularly those with a strong inflammatory component.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated neuron survival-promoting peptide, CHEC-7, consisting of the sequence of CHEASQC (SEQ ID NO: 3).

2. A pharmaceutical preparation comprising the neuron survival-promoting peptide of claim 1, in a biologically acceptable carrier.

3. A kit for treating a neurodegenerative disorder or inflammatory disorder in a patient comprising:
   a) an isolated CHEC-7 peptide consisting of the sequence of CHEASQC (SEQ ID NO: 3);
   b) a pharmaceutical excipient; and optionally
   c) a vehicle for administration, such as a syringe or catheter;
   and instructional material.

4. The kit of claim 3, wherein the kit further comprises a detectable label.

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: Homo sapiens

<400> SEQUENCE: 1

Cys His Glu Ala Ser Ala Ala Gln Cys
1               5

<210> SEQ ID NO 2
<211> LENGTH: 9
<212> TYPE: PRT
<213> ORGANISM: Homo sapiens

<400> SEQUENCE: 2

Cys Ala His Ala Gln Ala Glu Ser Cys
1               5

<210> SEQ ID NO 3
<211> LENGTH: 7
<212> TYPE: PRT
<213> ORGANISM: Homo sapiens

```
<400> SEQUENCE: 3

Cys His Glu Ala Ser Gln Cys
1               5
```